(12) United States Patent
May et al.

(10) Patent No.: US 11,643,372 B2
(45) Date of Patent: *May 9, 2023

(54) METHOD OF USING METAL ORGANIC FRAMEWORK

(71) Applicant: PHILLIPS 66 COMPANY, Houston, TX (US)

(72) Inventors: Camille Malonzo May, Collinsville, TX (US); Jose Edgar Mendez-Arroyo, Bartlesville, OK (US); Jianhua Yao, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/500,120

(22) Filed: Oct. 13, 2021

(65) Prior Publication Data

US 2022/0111371 A1 Apr. 14, 2022
US 2022/0111371 A1 Apr. 14, 2022

Related U.S. Application Data

(60) Provisional application No. 63/091,060, filed on Oct. 13, 2020.

(51) Int. Cl.
*C07C 2/32* (2006.01)
*C01B 37/00* (2006.01)
(Continued)

(52) U.S. Cl.
CPC ............... *C07C 2/32* (2013.01); *B01J 27/188* (2013.01); *B01J 31/0225* (2013.01);
(Continued)

(58) Field of Classification Search
CPC ........ C07C 2/32; C07C 2/58; C07C 2531/06; C07C 2531/18; C07C 2531/22; B01J 27/188; B01J 31/0225; B01J 31/1691; B01J 35/1009; B01J 35/1014; B01J 35/1019; B01J 35/1023; B01J 35/1028; B01J 35/1038; B01J 35/1042; B01J 35/1047; B01J 37/0213; B01J 37/04; B01J 37/08; B01J 2231/20; B01J 2231/44; B01J 2531/48; B01J 2531/49; B01J 2531/62; B01J 2231/42; B01J 2531/0216; B01J 2540/32; B01J 31/2239; C01B 37/00;
(Continued)

(56) References Cited

U.S. PATENT DOCUMENTS 10,182,593 B2 * 1/2019 Bromberg ............ B01J 20/3208
10,287,304 B2 5/2019 Yaghi et al.
2019/0345078 A1 * 11/2019 Abdelrahman .......... B01J 29/82

OTHER PUBLICATIONS

Li et al. ("Heteropolyacid supported MOF fibers for oxidative desulfurization of fuel", Chemical Engineering Journal 388 (2020) 124325). (Year: 2020).*

(Continued)

*Primary Examiner* — Ali Z Fadhel
(74) *Attorney, Agent, or Firm* — Phillips 66 Company

(57) ABSTRACT

A process comprising a heterogenous reaction between a solid metal organic framework supported heteropolyacid catalyst and a hydrocarbon feed to form a modified hydrocarbon stream. The modified hydrocarbon stream comprises essentially of C6+ hydrocarbons.

13 Claims, 24 Drawing Sheets

(51) Int. Cl.
  *B01J 31/16* (2006.01)
  *C07F 7/00* (2006.01)
  *C07F 9/00* (2006.01)
  *C07C 2/58* (2006.01)
  *B01J 27/188* (2006.01)
  *B01J 35/10* (2006.01)
  *B01J 37/02* (2006.01)
  *B01J 37/04* (2006.01)
  *B01J 37/08* (2006.01)
  *B01J 31/02* (2006.01)

(52) U.S. Cl.
  CPC ....... *B01J 31/1691* (2013.01); *B01J 35/1009* (2013.01); *B01J 35/1014* (2013.01); *B01J 35/1019* (2013.01); *B01J 35/1023* (2013.01); *B01J 35/1028* (2013.01); *B01J 35/1038* (2013.01); *B01J 35/1042* (2013.01); *B01J 35/1047* (2013.01); *B01J 37/0213* (2013.01); *B01J 37/04* (2013.01); *B01J 37/08* (2013.01); *C01B 37/00* (2013.01); *C07C 2/58* (2013.01); *C07F 7/00* (2013.01); *C07F 9/00* (2013.01); *B01J 2231/20* (2013.01); *B01J 2231/44* (2013.01); *B01J 2531/48* (2013.01); *B01J 2531/49* (2013.01); *B01J 2531/62* (2013.01); *C01P 2006/16* (2013.01); *C07C 2531/06* (2013.01); *C07C 2531/18* (2013.01); *C07C 2531/22* (2013.01)

(58) Field of Classification Search
  CPC .... C07F 7/00; C07F 9/00; C07F 7/003; C07F 11/005; C01P 2006/16
  See application file for complete search history.

(56) References Cited

OTHER PUBLICATIONS

Zhang et al. ("Green and Facile Synthesis of Metal-Organic Framework Cu-BTC-Supported Sn (II)-Substituted Keggin Heteropoly Composites as an Esterification Nanocatalyst for Biodiesel Production", Nanocomposite for Biodiesel Production, Front. Chem., Mar. 18, 2020; Green and Sustainable Chemistry). (Year: 2020).*

Zhang et al. "Construction of a Keggin heteropolyacid/Ni-MOF catalyst for esterification of fatty acids"; RSC Adv., 2021, 11, 33416-33424). (Year: 2021).*

Bromberg et al. ("Heteropolyacid-Functionalized Aluminum 2 Aminoterephthalate Metal-Organic Frameworks as Reactive Aldehyde Sorbents and Catalysts", ACS Appl. Mater. Interfaces 2013, 5, 5468-5477). (Year: 2013).*

Mercedes Alvaro, Avelino Corma, Debashish Das, Vicente Fornes, Hermenegildo Garcia, "Nafion-Functionalized Mesoporous MCM-41 Silica Shows High Activity and Selectivity for Carboxylic Acid Esterification and Friedel-Crafts Acylation Reactions", Science Direct, Journal of Catalysis, 231 (2005) pp. 48-55.

Wei Shen, David Dube, Serge Kaliguine, "Alkylation of Isobutane/1-Butene Over Periodic Mesoporous Organosilica Functionalized with Perfluoroalkylsulfonic Acid Group", Catalysis Communications 10, (2008) pp. 291-294.

* cited by examiner $M_3O(OH)_3$ node in MIL series of MOFs, where an OH group is replaced by DABCO $M_3O(OH)_3$ node in MIL series of MOFs, where M can be Cr, Fe, Sc, Ti, or Al $Cu_2(OH)_2$ node in HKUST-1 MOF $M_6O_8(OH)_8$ node in NU-1000 MOF, where M can be Zr or Hf O  H  C  Zr or Hf  Cu  Cr, Fe, Ti, Sc, or Al  N

METHOD OF USING METAL ORGANIC FRAMEWORK

CROSS-REFERENCE TO RELATED APPLICATIONS

This application is a non-provisional application which claims the benefit of and priority to U.S. Provisional Application Ser. No. 63/091,060 filed Oct. 13, 2020, entitled "Methods of Selection, Forming, and Using Metal Organic Frameworks," which is hereby incorporated by reference in its entirety.

STATEMENT REGARDING FEDERALLY SPONSORED RESEARCH OR DEVELOPMENT

None.

FIELD OF THE INVENTION

Method of using metal organic framework

BACKGROUND OF THE INVENTION

Acid catalysts are critical for industrial hydrocarbon transformations. Reactions such as cracking, alkylation, isomerization, oligomerization and hydration/dehydration, which are important steps in the production of chemicals and fuels, are acid catalyzed. The acid strength requirement for the catalysts differ for these processes.

Solid acids are deemed easier to handle and more environmentally benign than liquid acids. Some important families of solid acid catalysts include zeolites, oxides, clays, and polymer resins. These catalyst families are under continuous development to achieve new reactivities and improve catalytic performance.

Metal-organic frameworks (MOFs) are emerging as a promising class of heterogeneous catalysts due to their unique physical and chemical properties including high surface area, adjustable pore structure, tunable element composition, and the potential for surface modification. MOFs are porous, crystalline materials made of alternating organic (linkers) and inorganic building units (nodes). Importantly, their well-defined molecular structure and chemical environment enable the catalytic conversion of complex feedstocks into products with high selectivity and high conversion. The interest in MOFs in the field of catalysis has been attributed to the ability of these materials to bridge the gap between homogenous and heterogenous catalysis. This is due to the ability of MOFs to recreate chemically precise catalytic active sites such as those found in homogenous catalysis in a heterogenous support. In recent years, acidic MOFs have attracted significant research interest because of their potential application in a large class of acid-catalyzed reactions, including isomerization, cyclization, biomass transformation, benzylation, and aromatic alkylation.

An important refinery process that requires high acid strength catalysts is olefin-paraffin alkylation. The alkylation process produces high-octane gasoline blend called alkylate by reacting light olefins ($C_2$-$C_4$) with isoparaffins ($C_4$-$C_5$). Most commonly, isobutane is reacted with olefins (butenes) derived from refinery fluid catalytic cracking units to produce a product that consists of $C_6$-$C_9$ branched paraffins. Out of all the desired products, trimethylpentanes (TMPs) are typically the primary component. TMPs have research octane numbers (RONs) of 100-109.6. Other lower-octane reaction products such as dimethylhexanes (DMHs) and dimethylpentanes are also present.

For alkylation, the current catalyst systems used in refineries are liquid hydrofluoric acid (HF) and sulfuric acid ($H_2SO_4$). These strong acids are required to promote the hydride transfer reaction between an isoparaffin and hydrocarbon carbocation. Alternative alkylation catalysts are of interest because of risks associated with traditional HF- and $H_2SO_4$-based alkylation. Catalysts such as zeolites, ionic liquids (ILs), heteropolyacids (HPAs), acidic resins, and sulfated transition metal oxides (TMOs) have been shown to catalyze alkylation, but technical challenges—including low activity and rapid deactivation—exist.

Similarly, to alkylation, oligomerization is a hydrocarbon upgrading process that is an attractive, low-cost means to lower the vapor pressure of light naphtha streams that may be orphaned by future regulatory standards. This process can take olefins in the gas phase ($C_2$-$C_4$) and convert them to heavier liquid hydrocarbons suitable to a large array of applications such as: naphtha ($C_6$-$C_9$), diesel ($C_9$-$C_{12}$), jet fuel ($C_{12}$-$C_{16}$) and specialty chemicals. In order to undergo oligomerization, a source of acidity is also required much like in alkylation chemistry. This is due because both reactions sharing a common intermediate which is a carbocation formed when an olefin is protonated and stabilized in the surface of the catalyst. In oligomerization, there is no requirement for hydride transfer in the reaction mechanism allowing the process to occur with lower acidity requirements as compared to alkylation. Nevertheless, an important correlation exists wherein the smaller the olefin, the higher the acidity required to oligomerize the feed. Thus, high acidity materials have a larger operating window since they can utilize a wider range of feeds.

Materials for oligomerization can be found in the literature and often overlap with materials used for alkylation due to the shared chemical intermediates between both processes. These materials include: Aluminosilicates, zeolites, ionic liquids (ILs), heteropolyacids (HPAs), acidic resins, and sulfated transition metal oxides (TMOs). Despite the broad range of materials a diverse set of challenges exist. In many cases fast deactivation is observed due to formation of large oligomers that block the channels of materials and high conversion often is accompanied by poor selectivity to the desired products.

BRIEF SUMMARY OF THE DISCLOSURE

A process comprising a heterogenous reaction between a solid metal organic framework supported heteropolyacid catalyst and a hydrocarbon feed to form a modified hydrocarbon stream. The modified hydrocarbon stream comprises essentially of C6+ hydrocarbons.

A process comprising a heterogenous reaction between a solid metal organic framework supported heteropolyacid catalyst and a liquid hydrocarbon feed, consisting essentially of $C_2$ to $C_5$ hydrocarbons, to form a modified hydrocarbon stream. The modified hydrocarbon stream comprises essentially of C6+ hydrocarbons.

BRIEF DESCRIPTION OF THE DRAWINGS

A more complete understanding of the present invention and benefits thereof may be acquired by referring to the follow description taken in conjunction with the accompanying drawings in which.

DETAILED DESCRIPTION

Figure 1:
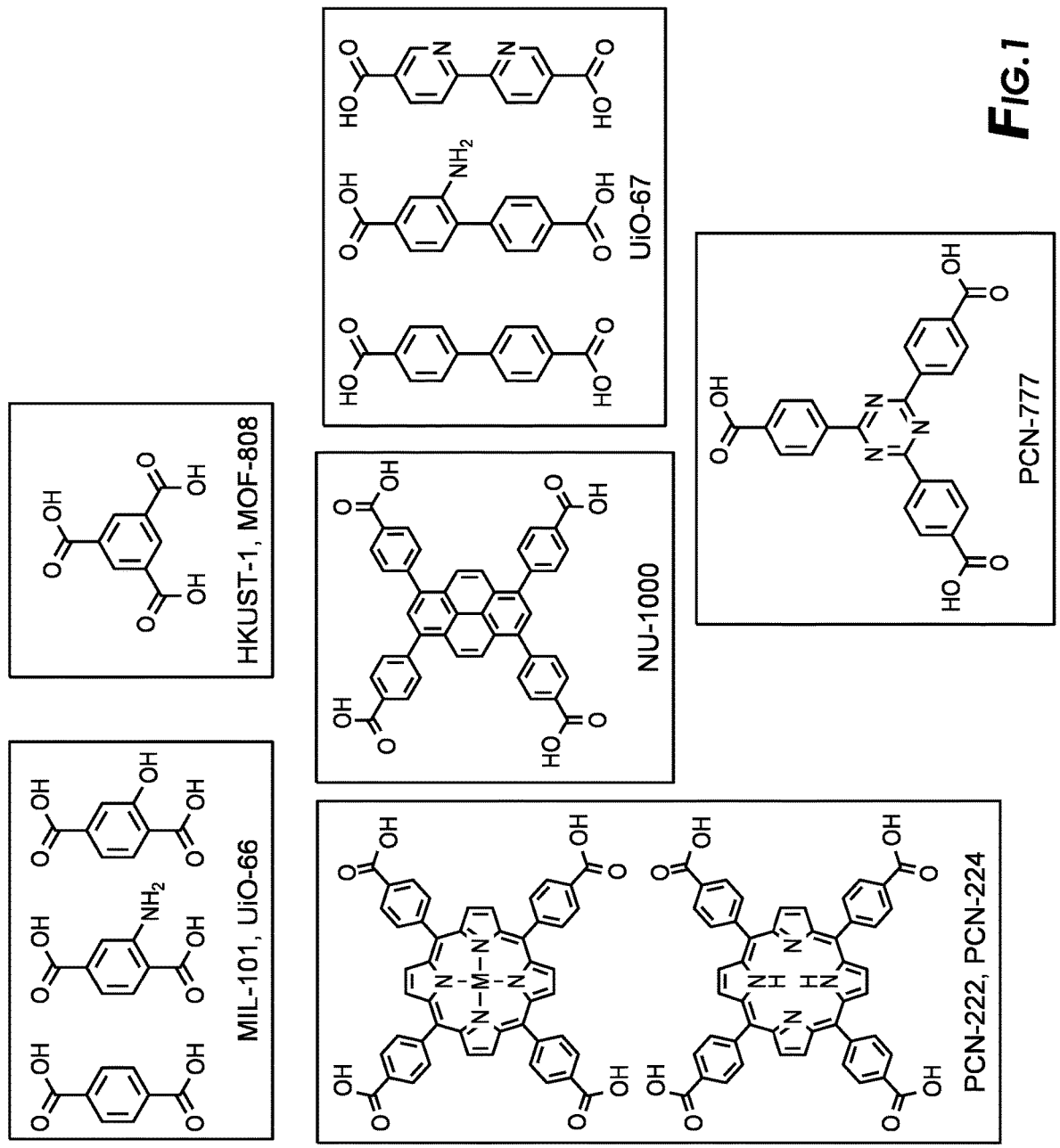
FIG. 1 depicts linkers currently used to build MOFs.

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

A process comprising a heterogeneous reaction between a hydrocarbon feed on a solid metal-organic framework-supported or based catalyst to form a modified hydrocarbon stream comprising essentially of $C_{6+}$ hydrocarbons. Non-limiting examples of MOFs-supported catalytically active components that can be used include heteropolyacids, sulfonic acids, oxyanions such as oxyanions-modified metal oxides, and ionic-type functionalities.

This arrangement details the preparation of different types of acidic MOF-based catalysts and their applications. The MOF-based catalysts can consist of two components: the MOF support and the acid sites that are bound to the MOF support. The acid sites can dictate the acid strength and therefore the type of reaction that can be catalyzed by the MOF based catalysts. Different acid sites require different binding motifs on the MOF support. The acid site can be encapsulated in the pore space of the MOF, or it could be bound to the MOF by attachment to the MOF node, linker or any non-linker ligand present in the MOF structure. The acid sites can be incorporated in the MOF support during the synthesis of the MOF, or they can be introduced to the MOF post-synthesis. The MOF support can influence mass diffusion, acid site dispersion and environment related to catalytic activity.

In a non-limiting example, the MOF support features a suitable pore and aperture size to encapsulate the acid species.

In a non-limiting example, the MOF support features nucleophilic groups such as hydroxyl, amino, thiol, and phosphine, among others. These groups can serve as attachment points for the acid species.

In a non-limiting example, the MOF support features a suitable metal oxide-based node that interacts with an anionic species to form an acid site.

In other non-limiting examples, the catalytically active components can be added to the solid metal organic frameworks via solution impregnation, one-pot synthesis, encapsulation, adsorption, deposition, grafting and/or covalent attachment reactions.

In one embodiment the loading of the catalytic active components on the solid metal organic framework can be greater than 5% by weight, or in other embodiments even 10%, 15%, 20%, 25%, 30%, 35%, 40%, 45%, 50%, 55%, 60%, 65%, even 70% or more by weight.

In addition, this arrangement describes the composition of a new family of acidic MOFs bearing halogenated and/or non-halogenated sulfonic acid functionalities as acid sites for use as alternative solid acid catalysts for different organic transformations. The reactivity of this family of MOFs can be tuned by changing the type of MOF and sulfonic acid functionality to meet catalytic application demands. In one example, the sulfonic acid functionalized MOF has enough strength to catalyze the olefin-paraffin alkylation reaction.

The heterogeneous reaction can be either an olefin-paraffin alkylation reaction or an olefin oligomerization reaction. As an example, for some alkylation reactions, the hydrocarbon component produced is a $C_{6+}$ paraffinic hydrocarbon. As another example, for some oligomerization reactions, the hydrocarbon component produced is a $C_{6+}$ olefinic hydrocarbon or even an $C_{8+}$ olefinic hydrocarbon.

In one embodiment, the hydrocarbon feed comprises and/or comprises essentially of $C_2$ to $C_5$ hydrocarbons such as light hydrocarbons. These light hydrocarbons feed can be olefins such as propylene, butylene and/or isoparaffins such as isobutane. In another embodiment, the heterogenous reaction between a solid metal organic framework and a hydrocarbon feed which can be a gaseous hydrocarbon feed, a liquid hydrocarbon feed, or a supercritical hydrocarbon feed.

In this arrangement, we describe a process that uses an acidic MOF that can convert a hydrocarbon feed of light olefins ($C_3$-$C_6$) and isoparaffins ($C_4$-$C_5$) to heavier, more valuable products, such as alkylate which is a blend stock for high octane gasoline. This product effluent is forecasted to have great growth potential despite the forecasted changes in gasoline demand. In the refining process many of these hydrocarbon feeds or light olefins (especially C4s) end up as feedstock for processes such as alkylation which can produce valuable alkylate, such as high octane gasoline components.

In this arrangement we describe a new process that uses an acidic MOF that can selectively oligomerize a hydrocarbon feed of light olefins ($C_3$-$C_6$) to heavier more valuable products such as the modified hydrocarbon stream which can be high octane gasoline, low sulfur diesel, jet fuel, specialty solvents or synthetic lube oils, which have been forecast to have great growth potential despite the forecasted changes in gasoline demand.

In another embodiment, the proposed arrangement utilizes the high selectivity of the MOF material and engineered conditions to integrate oligomerization and alkylation to maximize the value of the product stream. In this integrated process, the low value olefins are selectively oligomerized while the high value olefins are alkylated to form high octane gasoline components.

In a non-limiting embodiment, the process is able to achieve a modified hydrocarbon stream with a conversion rate of $C_6+$ hydrocarbons at a rate greater than 20%, 25%, 30%, 35%, 40%, 45%, 50%, 55%, even greater than 60%.

In a non-limiting embodiment, the process is able to achieve a modified hydrocarbon stream with a selectivity rate of $C_6+$ hydrocarbons at a rate greater than 20%, 25%, 30%, 35%, 40%, 45%, 50%, 55%, even greater than 60%.

Other potential applications for acid MOFs include olefin oligomerization, $C_2$-$C_4$ olefins/i-$C_4$ and i$C_5$ isoparaffin alkylation, olefin isomerization, and olefin/aromatic alkylation.

MOF Supports

MOB are built up of metal cation containing nodes bridged by organic linkers. Non-limiting examples of linkers and nodes that can be used are generally described below.

MOF Linkers and Non-Linker Ligands

The organic linkers of the MOFs of the arrangement may be any linker molecule or molecule combination capable of binding to at least two inorganic nodes and comprising an organic moiety. Thus, the linker may be any of the linkers conventionally used in MOF production. These are generally compounds with at least two node-binding groups, e.g. carboxylates, optionally with extra functional groups which do not bind the nodes but may bind metal ions on other materials it is desired to load into the MOF. The linkers moreover typically have rigidifying groups between the node-binding groups to facilitate 3D MOF formation. Examples of suitable organic linker compounds include oxalic acid, ethyloxalic acid, fumaric acid, 1,3,5-benzene tricarboxylic acid (BTC), 1,3,6,8-tetrakis(p-benzoic acid) pyrene (TBAPy), 1,3,5-benzene tribenzoic acid (BTB), DCPB, benzene tribiphenylcarboxylic acid (BBC), 5,15-bis (4-carboxyphenyl) zinc (II) porphyrin (BCPP), 1,4-benzene dicarboxylic acid (BDC), 2-amino-1,4-benzene dicarboxylic acid (R3-BDC or H2N BDC), 1,1'-azo-diphenyl 4,4'-dicarboxylic acid, cyclobutyl-1,4-benzene dicarboxylic acid (R6-BDC), benzene tricarboxylic acid, 2,6-naphthalene dicarboxylic acid (NDC), 1,1'-biphenyl 4,4'-dicarboxylic acid (BPDC), 2,2'-bipyridyl-5,5'-dicarboxylic acid, adamantane tetracarboxylic acid (ATC), adamantane dibenzoic acid (ADB), adamantane teracarboxylic acid (ATC), dihydroxyterephthalic acid (DHBDC), biphenyltetracarboxylic acid (BPTC), tetrahydropyrene 2,7-dicarboxylic acid (HPDC), dihydroxyterephthalic acid (DHBC), pyrene 2,7-dicarboxylic acid (PDC), pyrazine dicarboxylic acid, acetylene dicarboxylic acid (ADC), camphor dicarboxylic acid, fumaric acid, benzene tetracarboxylic acid, 1,4-bis(4-carboxyphenyl)butadiyne, nicotinic acid, and terphenyl dicarboxylic acid (TPDC). Other acids besides carboxylic acids, e.g. boronic acids may also be used. A mixture of linkers may be used to introduce functional groups within the pore space, e.g. by using aminobenzoic acid to provide free amine groups or by using a shorter linker such as oxalic acid.

In one embodiment, the linker comprises an organic-based parent chain comprising alkyl, hetero-alkyl, alkenyl, hetero-alkenyl, alkynyl, hetero-alkynyl, one or more cycloalkyl rings, one or more cycloalkenyl rings, one or more cycloalkynyl rings, one of more aryl rings, one or more heterocycle rings, or any combination of the preceding groups, including larger ring structures composed of linked and/or fused ring systems of different types of rings; wherein this organic-based parent chain may be further substituted with one or more functional groups, including additional substituted or unsubstituted hydrocarbons and heterocycle groups, or a combination thereof; and wherein the linker contains at least one (e.g. 1, 2, 3, 4, 5, 6, ... ) linking cluster.

In a yet further embodiment, the linker of the metal organic framework has an organic-based parent chain that is comprised of one or more substituted or unsubstituted rings; wherein one or more of these rings are further substituted with one or more functional groups, including additional substituted or unsubstituted hydrocarbons and heterocycle groups, or a combination thereof; and wherein the linker contains at least one (e.g., 1, 2, 3, 4, 5, 6, or more) linking cluster that is either a carboxylic acid, amine, thiol, cyano, nitro, hydroxyl, or heterocycle ring heteroatom, such as the N in pyridine.

In another embodiment, the linker of the metal organic framework has an organic-based parent chain that is comprised of one or more substituted or unsubstituted rings; wherein one or more of these rings are further substituted with one or more functional groups, including additional substituted or unsubstituted hydrocarbons and heterocycle groups, or a combination thereof; and wherein the linker contains at least one (e.g., 1, 2, 3, 4, 5, 6, or more) carboxylic acid linking cluster.

The non-linker ligands of the MOFs of the arrangement may be any ligand molecule or molecule combination capable of binding to one inorganic node and comprising an organic moiety. These are generally compounds with one node-binding group, e.g. carboxylates, with or without extra functional groups that do not bind the nodes but may react with and/or bind other species such as electrophiles and acid site precursors that are desired to be used to functionalize the MOF.

In a certain embodiment the pore aperture of the MOF support is controlled by the length of the linker.

MOF Nodes

The inorganic nodes of MOFs can be synthesized using metal ions having distinctly different coordination geometries, in combination with a ligand possessing multidentate functional groups, and a suitable templating agent. In general, the inorganic nodes could be one or more metal-based nodes from Group 1 through 16 metals of the IUPAC Periodic Table of the Elements including actinides, and lanthanides, and combinations thereof. Examples of metal ions in the node can include: $Mg^{2+}$, $Ca^{2+}$, $Sr^{2+}$, $Ba^{2+}$, $Sc^{3+}$, $Y^{3+}$, $Ti^{4+}$, $Zr^{4+}$, $Ce^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{3+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{2+}$, $As^{3+}$, $As^+$, $Sb^{5+}$, $Sb^{3+}$, $Sb^+$, and $Bi^{5+}$, $Bi^{3+}$, $Bi^+$; along with the corresponding metal salt counteranion. As used herein, the nodes refer to both metal and metalloid ions. Generally, the nodes that can be useful include: $Sc^{3+}$, $Zr^{4+}$, $Ce^{4+}$, $Hf^{4+}$, $Ti^{4+}$, $V^{4+}$, $V^{3+}$, $V^{2+}$, $Cr^{3+}$, $Mo^{3+}$, $Mn^{3+}$, $Mn^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^{2+}$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Al^{3+}$, $Ga^{3+}$, $In^{3+}$, $Ge^{4+}$, $Ge^{2+}$, $Sn^{4+}$, $Sn^{2+}$, $Pb^{4+}$, $Pb^{2+}$, $Sb^{5+}$, $Sb^{3+}$, $Sb^+$, and $Bi^{5+}$, $Bi^{3+}$, $Bi^+$; along with the corresponding metal salt counteranion. A preferred group of nodes includes: $Sc^{3+}$, $Zr^{4+}$, $Ce^{4+}$, $Hf^{4+}$, $Ti^{4+}$, $V^{4+}$, $V^{3+}$, $Cr^{3+}$, $Mo^{3+}$, $Mn^{3+}$, $Mn^{2+}$, $Fe^{3+}$, $Fe^{2+}$, $Co^3$, $Co^{2+}$, $Ni^{2+}$, $Ni^+$, $Cu^{2+}$, $Cu^+$, $Ag^+$, $Zn^{2+}$, $Cd^{2+}$, $Al^{3+}$, $Sn^{4+}$, $Sn^{2+}$, and $Bi^{5+}$, $Bi^{3+}$, $Bi^+$; along with the corresponding metal salt counteranion. More preferably the nodes used are selected from the group consisting of: $Zr^{4+}$, $Ce^{4+}$, $Hf^{4+}$, $Cr^{3+}$, $Mn^{3+}$, $Mn^{2+}$, $Fe^{3+}$, $Fe^{2+}$, $Co^{3+}$, $Co^{2+}$, $Ni^{2+}$, $Ni^+$, $Cu^{2+}$, $Cu^+$, $Ag^+$, $Zn^{2+}$, $Cd^{2+}$, $Al^{3+}$ along with the corresponding metal salt counteranion. Most preferably the nodes useful in this arrangement are selected from the group consisting of: $Zr^{4+}$, $Ce^{4+}$, $Hf^{4+}$, $Cr^{3+}$, $Fe^{3+}$, $Fe^{2+}$, $Co^{3+}$, $Co^{2+}$, $Ni^{2+}$, $Ni^+$, $Cu^{2+}$, $Cu^+$, $Zn^{2+}$, $Al^{3+}$ along with the corresponding metal salt counteranion. An especially preferred group of nodes that can be used include: $Zr^{4+}$, $Ce^{4+}$, $Hf^4$, $Cr^{3+}$, $Fe^{3+}$, $Co^{3+}$, $Co^{2+}$, $Ni^{2+}$, $Ni^+$, $Zn^{2+}$, $Al^{3+}$ along with the corresponding metal salt counteranion.

In yet another embodiment, one or more metals that can be used in the (1) synthesis of frameworks, (2) exchanged post synthesis of the frameworks, and/or (3) added to a framework by forming coordination complexes with post framework reactant functional group(s) include, but are not limited to, $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^+$, $Ti^{3+}$, $Ti^{2+}$, $Zr^{4+}$, $Zr^{3+}$, $Zr^{2+}$, $Hf^{4+}$, $Hf^+$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, Cr, $Mo^{6+}$, $Mo^{5+}$, $Mo^{4+}$, $Mo^{3+}$, $Mo^{2+}$, Mo+, Mo, $W^{6+}$, $W^5$, $W^{4+}$, $W^{3+}$, $W^{2+}$, W+, W, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^5$, $Re^{4+}$, $Re^{3+}$, $Re^{2+}$, Re+, Re, $Fe^{6+}$, $Fe^{4+}$, $Fe^{3+}$, $Fe^{2+}$, $Fe^+$, Fe, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, Os, $Co^{5+}$, $Co^{4+}$, $Co^{33}$, $Co^{2+}$, $Co^+$, $Rh^{6+}$, $Rh^{5+}$, $Rh^{4+}$, $Rh^{3+}$, $Rh^{2+}$, Rh+, $Ir^{6+}$, $Ir^{5+}$, $Ir^{4+}$, $Ir^{3+}$, $Ir^{2+}$, Ir+, Ir, $Ni^{3+}$, $Ni^{2+}$, Ni+, Ni, $Pd^{6+}$, $Pd^{4+}$, $Pd^{2+}$, Pd+, Pd, $Pt^{6+}$, $Pt^{5+}$, $Pt^{4+}$, $Pt^{3+}$, $Pt^{2+}$, Pt+, $Cu^{4+}$, $Cu^{3+}$, $Cu^{2+}$, $Cu^+$, $Ag^{3+}$, $Ag^{2+}$, Ag+, $Au^{5+}$, $Au^{4+}$, $Au^{3+}$, $Au^{2+}$, Au+, $Zn^{2+}$, $Zn^+$, Zn, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, Al+, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, Ge, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, Gd+, $Tb^{4+}$, $Tb^{3+}$, $Tb^{2+}$, $Tb^+$, $db^{3+}$, $db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, and any combination thereof, along with corresponding metal salt counter-anions.

Preparation of MOF Supports

The preparation of the MOFs in the disclosure can be carried out in either an aqueous, non-aqueous solvents or in a solvent-free system. The solvent may be polar or nonpolar, or a combination thereof, as the case may be. The reaction mixture or suspension comprises a solvent system, linker or moieties, and a metal or a metal/salt complex. The reaction solution, mixture or suspension may further contain a templating agent, growth modulator or other non-linker ligands, catalytically active component or combinations thereof. The reaction mixture may be heated at an elevated temperature or maintained at ambient temperature, depending on the reaction components.

Examples of non-aqueous solvents that can be used in the reaction to make the MOF and/or used as non-aqueous solvent for a post synthesized MOF reaction, include, but is not limited to: n-hydrocarbon based solvents, such as pentane, hexane, octadecane, and dodecane; branched and cyclo-hydrocarbon based solvents, such as cycloheptane, cyclohexane, methyl cyclohexane, cyclohexene, cyclopentane; aryl and substituted aryl based solvents, such as benzene, toluene, xylene, chlorobenzene, nitrobenzene, cyanobenzene, naphthalene, and aniline; mixed hydrocarbon and aryl based solvents, such as, mixed hexanes, mixed pentanes, naptha, and petroleum ether; alcohol based solvents, such as, methanol, ethanol, n-propanol, isopropanol, propylene glycol, 1,3-propanediol, n-butanol, isobutanol, 2-methyl-1-butanol, tert-butanol, 1,4-butanediol, 2-methyl-1-pentanol, and 2-pentanol; amide based solvents, such as, dimethylacetamide, dimethylformamide (DMF), diethylformamide (DEF), formamide, N-methylformamide, N-methylpyrrolidone, and 2-pyrrolidone; amine based solvents, such as, piperidine, pyrrolidine, collidine, pyridine, morpholine, quinoline, ethanolamine, ethylenediamine, and diethylenetriamine; ester based solvents, such as, butylacetate, sec-butyl acetate, tert-butyl acetate, diethyl carbonate, ethyl acetate, ethyl acetoacetate, ethyl lactate, ethylene carbonate, hexyl acetate, isobutyl acetate, isopropyl acetate, methyl acetate, propyl acetate, and propylene carbonate; ether based solvents, such as, di-tert-butyl ether, diethyl ether, diglyme, diisopropyl ether, 1,4-dioxane, 2-methyltetrahydrofuran, tetrahydrofuran (THF), and tetrahydropyran; glycol ether based solvents, such as, 2-butoxyethanol, dimethoxyethane, 2-ethoxyethanol, 2-(2-ethoxyethoxy)ethanol, and 2-methoxyethanol; halogenated based solvents, such as, carbon tetrachloride, chlorobenzene, chloroform, 1,1-dichloroethane, 1,2-dichloroethane, 1,2-dichloroethene, dichloromethane (DCM), diiodomethane, epichlorohydrin, hexachlorobutadiene, hexafluoro-2-propanol, perfluorodecalin, perfluorohexane, tetrabromomethane, 1,1,2,2-tetrachloroethane, tetrachloroethylene, 1,3,5-trichlorobenzene, 1,1,1-trichloroethane, 1,1,2-trichloroethane, trichloroethylene, 1,2,3-trichloropropane, trifluoroacetic acid, and 2,2,2-trifluoroethanol; inorganic based solvents, such as hydrogen chloride, ammonia, carbon disulfide, thionyl chloride, and phosphorous tribromide; ketone based solvents, such as, acetone, butanone, ethylisopropyl ketone, isophorone, methyl isobutyl ketone, methyl isopropyl ketone, and 3-pentanone; nitro and nitrile based solvents, such as, nitroethane, acetonitrile, and nitromethane; sulfur based solvents, dimethyl sulfoxide (DMSO), methylsulfonylmethane, sulfolane, isocyanomethane, thiophene, and thiodiglycol; urea, lactone and carbonate based solvents, such as 1-3-dimethyl-3,4,5,6-tetrahydro-2(1H)-pyrimidinone (DMPU), 1-3-dimethyl-2-imidazolidinone, butyrolactone, cis-2,3-butylene carbonate, trans-2,3-butylene carbonate, 2,3-butylene carbonate; green solvents such as cyrene and valerolactone; ionic liquids; carboxylic acid based solvents, such as formic acid, acetic acid, chloracetic acid, trichloroacetic acid, trifluoroacetic acid, propanoic acid, butanoic acid, caproic acid, oxalic acid, and benzoic acid; boron and phosphorous based solvents, such as triethyl borate, triethyl phosphate, trimethyl borate, and trimethyl phosphate; deuterium containing solvents, such as deuterated acetone, deuterated benzene, deuterated chloroform, deuterated dichloromethane, deuterated DMF, deuterated DMSO, deuterated ethanol, deuterated methanol, and deuterated THF; and any appropriate mixtures thereof.

In another embodiment, the nonaqueous solvent used as the solvent system in synthesizing the MOF has a pH less than 7. In a further embodiment, the solvent system used to synthesize the MOF is an aqueous solution that has a pH less than 7. In yet a further embodiment, the solvent system used to synthesize the frameworks contains water. In another embodiment, the solvent system used to synthesize the frameworks contains water and hydrochloric acid.

Those skilled in the art will be readily able to determine an appropriate solvent or appropriate mixture of solvents based on the starting reactants and/or where the choice of a particular solvent(s) is not believed to be crucial in obtaining the materials of the disclosure.

In a certain embodiment, crystallization of the frameworks can be improved by adding an additive that promotes nucleation.

In a certain embodiment, the solution, mixture or suspension is maintained at ambient temperature to allow for crystallization. In another embodiment, the solution, mixture, or suspension is heated in isothermal oven for up to 300° C. to allow for crystallization. In yet another embodiment, activated frameworks can be generated by calcination. In a further embodiment, calcination of the frameworks can be achieved by heating the frameworks at 350° C. for at least 1 hour.

In a certain embodiment, the MOF is synthesized in a solvent-free system through mechanical mixing such as ball milling or grinding of the reaction mixture comprised of the linker or moieties, and a metal or a metal/salt complex. The reaction mixture may further contain a templating agent, growth modulator or other non-linker ligands, catalytic active component or combinations thereof. The reaction mixture may be heated at an elevated temperature or maintained at ambient temperature, depending on the reaction components.

After the MOFs are synthesized, the MOFs may be further modified by reacting with one or more post MOF reactants that may or may not have denticity. In a certain embodiment, the frameworks as-synthesized are not reacted with a post framework reactant. In another embodiment, the frameworks as-synthesized are reacted with at least one post framework reactant. In yet another embodiment, the frameworks as-synthesized are reacted with at least two post framework reactants. In a further embodiment, the frameworks as-synthesized are reacted with at least one post framework reactant that will result in adding denticity to the framework.

It is contemplated by this disclosure that chemical reactions that modify, substitute, or eliminate a functional group post-synthesis of the MOF with post framework reactant may use one or more similar or divergent chemical reaction mechanisms depending on the type of functional group and/or post framework reactant used in the reaction. Examples of chemical reaction mechanisms contemplated by this arrangement include, but is not limited to, radical-based, unimolecular nucleophilic substitution (SN1), bimolecular nucleophilic substitution (SN2), unimolecular elimination (E1), bimolecular elimination (E2), E1cB elimination, nucleophilic aromatic substitution (SnAr), nucleophilic internal substitution (SNi), nucleophilic addition, electrophilic addition, oxidation, reduction, cycloaddition, ring closing metathesis (RCM), pericylic, electrocylic, rearrangement, carbene, carbenoid, cross coupling, and degradation.

It is yet further contemplated by this disclosure that to enhance chemoselectivity, it may be desirable to protect one or more functional groups that can generate unfavorable products upon a chemical reaction desired for another functional group, and then deprotect this protected group after the desired reaction is completed. Employing such a protection/deprotection strategy could be used for one or more functional groups.

Other agents can be added to increase the rate of the MOF formation reactions disclosed herein, including adding catalysts, bases, and acids.

In another embodiment, the post framework reactant is selected to have a property selected from the group comprising, binds a metal ion, increases the hydrophobicity of the framework, decreases the hydrophobicity of the framework, modifies the chemical sorption of the framework, modifies the pore size of the framework, and tethers a catalyst to the framework.

In one embodiment, the post framework reactant can be a saturated or unsaturated heterocycle.

In another embodiment, the post framework reactant has 1-100 atoms with functional groups including atoms such as N, S, O, P and transition metals.

In yet another embodiment, the post framework reactant is selected to modulate the size of the pores in the framework.

In another embodiment, the post framework reactant is selected to increase the hydrophobicity of the framework. In an alternative embodiment, the post framework reactant is selected to decrease the hydrophobicity of the framework.

In yet another embodiment, the post framework reactant is selected to modulate chemical, inorganic and/or organic sorption of the framework.

In yet another embodiment, the post framework reactant is selected to modulate gas separation of the framework. In a certain embodiment, the post framework reactant creates an electric dipole moment on the surface of the framework when it chelates a metal ion.

In a further embodiment, the post framework reactant is selected to modulate the gas sorption properties of the framework. In another embodiment, the post framework reactant is selected to promote or increase hydrocarbon gas sorption of the framework.

In yet a further embodiment, the post framework reactant is selected to increase or add catalytic efficiency to the framework.

In another embodiment, a post framework reactant is selected so that organometallic complexes can be tethered to the framework. Such tethered organometallic complexes can be used, for example, as heterogeneous catalysts.

To improve MOF catalyst usage the following are possible ways to improve the MOF and or determine the best possible MOF support to utilize. The organic linkers and nodes could be selected to achieve MOFs with large pore size and improve the diffusion of reactants and reagents through the MOF catalyst, improving catalyst life. Growth modulators could be used to create defects in the MOF structure to also improve diffusion and catalyst life. Synthetic modification of the organic linker could be done to increase the hydrophobicity of the MOF. This increases the local concentration of desired reactant molecules around the acid sites and optimize catalyst selectivity. Aside from the MOF nodes and linkers, non-linker ligands could be used as attachment points for acid sites, which expands the types of MOF supports that could be used to make the acid MOF catalysts. It is envisioned that by using some or all of the parameters above one can be able to select MOFs for improved alkylation and/or oligomerization catalytic activity.

Examples of MOFs

The following additional examples of certain embodiments of the invention are given. Each example is provided by way of explanation of the invention, one of many embodiments of the invention, and the following examples should not be read to limit, or define, the scope of the invention.

Table 1 below lists some exemplary MOFs that are currently used

TABLE 1

| Name | Nodecomp. | Topology | Chanel Type | Pore Size (Å) |
|---|---|---|---|---|
| HKUST-1 | Cu | tbo | 3D | 12 |
| MIL-101 | Al, Fe, Cr | mtm | 3D | 16, 29, 34 |
| UiO-66 | Zr, Hf, Ce | fcu | 3D | 8 |

TABLE 1-continued

| Name | Nodecomp. | Topology | Chanel Type | Pore Size (Å) |
|---|---|---|---|---|
| UiO-67 | Zr, Hf | fcu | 3D | 12 |
| MOF-808 | Zr, Hf, Ce | spn | 3D | 16 |
| PCN-777 | Zr, Hf | spn | 3D | 32 |
| PCN-224 | Zr, Hf | she | 1D | 20 |
| PCN-222 | Zr, Hf | csq | 1D | 37 |
| NU-1000 | Zr, Hf | csq | 1D | 31 |

The linkers currently used to build MOFs are shown in FIG. 1.

Non-limiting examples of ways to create acid sites in MOFs include the functionalization of metal nodes with oxyanions, encapsulating heteropolyacids on the MOFs, grafting sulfonic acids on the MOFs, or even immobilization of ionic liquids on MOFs. It is expected that individual physical tests can be run to determine the best MOFs for catalytic applications.

These acid MOFs can then be tested differently using methods such as: Oligomerization testing (for oligomerization activity and long term stability), Alkylation testing (for cracking activity, oligomerization activity, alkylation performance and stability), and Batch Reactor Testing (Testing for activity for isomerization, activity for alkylation and activity hydride transfer).

Example 1

Ionic Liquids in MOFs

For MOF-supported Ionic Liquids (ILs), the anchor point could be the metal node or a functional group on the linker. ILs are salts with a low melting point, typically less than 100° C. The origin of the low melting point is the charge delocalization in its bulky constituent ions, leading to small lattice enthalpies and large entropy changes that favor melting. The variety of choices for cations and anions provides a high synthetic flexibility for ILs, and this flexibility is magnified by the ability to make IL mixtures.

ILs can display Lewis or Brønsted acidity or both. Most of the known Lewis acidity comes from the electron-pair-accepting ability of the anion, while Brønsted acidity can come from the cation and/or the anion. Additional Brønsted sites such as —$SO_3H$ can also be introduced through alkyl side chains tethered to the ionic core.

For alkylation, ILs containing multinuclear halometallate anions such as $[Al_2Cl_7]^-$ are highly active and are thus among the synthetic targets for MOF-based alkylation catalyst in this invention.

Example 2

MOF-Supported Heteropolyacids

Heteropolyacids (HPAs), specifically phosphotungstic acid (PTA), had been encapsulated in MOF pores. MOFs used to host $H_3PW_{12}O_{40}$ include MIL-100, MIL-101, UiO-67, NU-1000, HKUST-1, ZIF-67 and ZIF-8. HPAs are solid acids that incorporate transition metal-oxygen clusters as anions. They are called the Keggin and Wells-Dawson structures, and like other HPA anions, they feature metal-oxygen octahedra as a basic structural unit. The most common metals that make up the octahedra are tungsten, molybdenum, and vanadium. The anion is formed when these octahedra surround one or more heteroatoms, which are often phosphorous or silicon. The acidity of HPAs is purely Brønsted in nature. For the commercially available Keggin-type HPAs, the acid strength decreases in the order $H3PW12O40>H4SiW12O40>H3PMo12O40>H4SiMo12O40$. H3PW12O40 (called phosphotungstic acid, hereon referred to as PTA) was found to be more acidic than H2SO4 and is therefore a suitable acid site candidate to make acid MOF catalysts.

With MIL-101, the PTA loading could be as high as 60% by weight. The synthesis is also facile. PTA can be added to the MOF synthesis mixture in a one-pot type ship-around-bottle synthesis or it can be impregnated into the MOF post-synthesis. A common concern with supported PTA is the strong interaction between PTA and traditional supports like silica, which lowers the acidity of the former. The nature of the MOF building blocks gives it different surface properties, which can be tuned to minimize any effects on the acidity of encapsulated PTA In one embodiment, a metal organic framework composition can comprise a solid metal organic framework supported heteropolyacid wherein the heteropolyacid loading is greater than 25% by weight and the pore volume is less than 2 mL/g. In one non-limiting embodiment, the composition can be formed by forming a solution containing a heteropolyacid and a solvent to form a heteropolyacid solution, soaking a metal organic framework in the heteropolyacid solution to form an impregnated metal organic framework, and drying the impregnated metal organic framework to form a solid metal organic framework supported heteropolyacid. In another non-limiting embodiment, the composition can be formed by mixing a solution of solid metal organic framework starting reagents and a heteropolyacid to form a starting solution and reacting the starting solution in a reactor to form a solid metal organic framework supported heteropolyacid.

In one non-limiting embodiment, the pore volume of the solid metal organic framework supported heteropolyacid is less than 2 mL/g. In another non-limiting embodiment, the BET surface area of the solid metal organic framework supported heteropolyacid is less than 4,500 m$^2$/g.

Non-limiting examples of HPAs include $H_3PW_{12}O_{40}$, $H_3PMo_{12}O_{40}$, $H_3SiW_{12}O_{40}$, $H_6P_2Mo_{18}O_{62}$.

The process of a reaction can be a heterogenous reaction between a solid metal organic framework supported heteropolyacid catalyst and a hydrocarbon feed. This modified hydrocarbon stream can comprise essentially of $C_{6+}$ hydrocarbons.

Preparation of HPA Materials:

PTA. The reference PTA catalyst was prepared heat-treating phosphotungstic acid hydrate at 300° C. to dehydrate the sample prior to catalyst testing.

Silica-supported PTA catalyst (PTA@SiO$_2$). This reference catalyst was prepared via solution impregnation. Silica gel was immersed in a solution of PTA in H$_2$O. The solid was separated by filtration and dried in a vacuum oven.

MIL-101. The MIL-101 MOF used as support for PTA was synthesized by dissolving Cr(NO$_3$)$_3$.9H$_2$O in an aqueous solution of HNO$_3$. Terephthalic acid was then added. The MOF synthesis was then carried out in a Parr reactor at a suitable temperature for MOF formation. The product, MIL-101, was washed with H$_2$O and ethanol prior to air-drying.

MIL-101-supported PTA prepared via solution impregnation. Two samples were prepared as follows: (1) A solution of PTA in H$_2$O was first prepared. MIL-101 was immersed in this solution. The solid was separated by centrifugation, air-dried and then dried in an oven. This sample is denoted as imp-PTA@MIL-101. (2) The second sample was prepared using the same procedure as (1), except the pH of the PTA solution was adjusted by using an aqueous solution of HNO$_3$. This sample is denoted as imp-PTA@MIL-101-pH.

MIL-101-supported PTA prepared via one-pot synthesis. Two samples with different PTA loadings were prepared. The same synthesis as MIL-101 was followed except PTA was dissolved in the reaction mixture prior to loading into the Parr reactor. Different PTA loadings were achieved by varying the amount of PTA added to the MIL-101 reaction mixture. The samples are denoted as op-PTA@MIL-101 and op-PTA@MIL-101-low, for the normal and lower loading samples, respectively.

Characterization of HPA Materials

The PTA loading and textural properties of the supported PTA samples were determined by XRF and N$_2$ physisorption analyses, respectively. Please see Table 2

TABLE 2

| Material Type | Material | Weight % PTA from XRF | BET Surface Area (m2/g) | Pore Volume (mL/g) |
|---|---|---|---|---|
| Support | silica gel | — | 474 | 0.91 |
| | MIL-101 | — | 3030 | 1.34 |
| Silica gel-supported PTA via wet impregnation | PTA@SiO$_2$ | 30 | 389 | 0.74 |
| MIL-101-supported PTA via wet impregnation | imp-PTA@MIL-101 | 62 | 711 | 0.34 |
| | imp-PTA@MIL-101-pH | 63 | 821 | 0.38 |
| MIL-101-supported PTA via one-pot synthesis | op-PTA@MIL-101 | 65 | 720 | 0.35 |
| | op-PTA@MIL-101-low | 34 | 1963 | 0.93 |

The PTA loading for the reference PTA@SiO$_2$ sample was 30%, which is enough to disperse a monolayer of PTA on the surface of the silica support. High PTA loadings in MIL-101 (34 to 65% by weight) were achieved.

Figure 2:
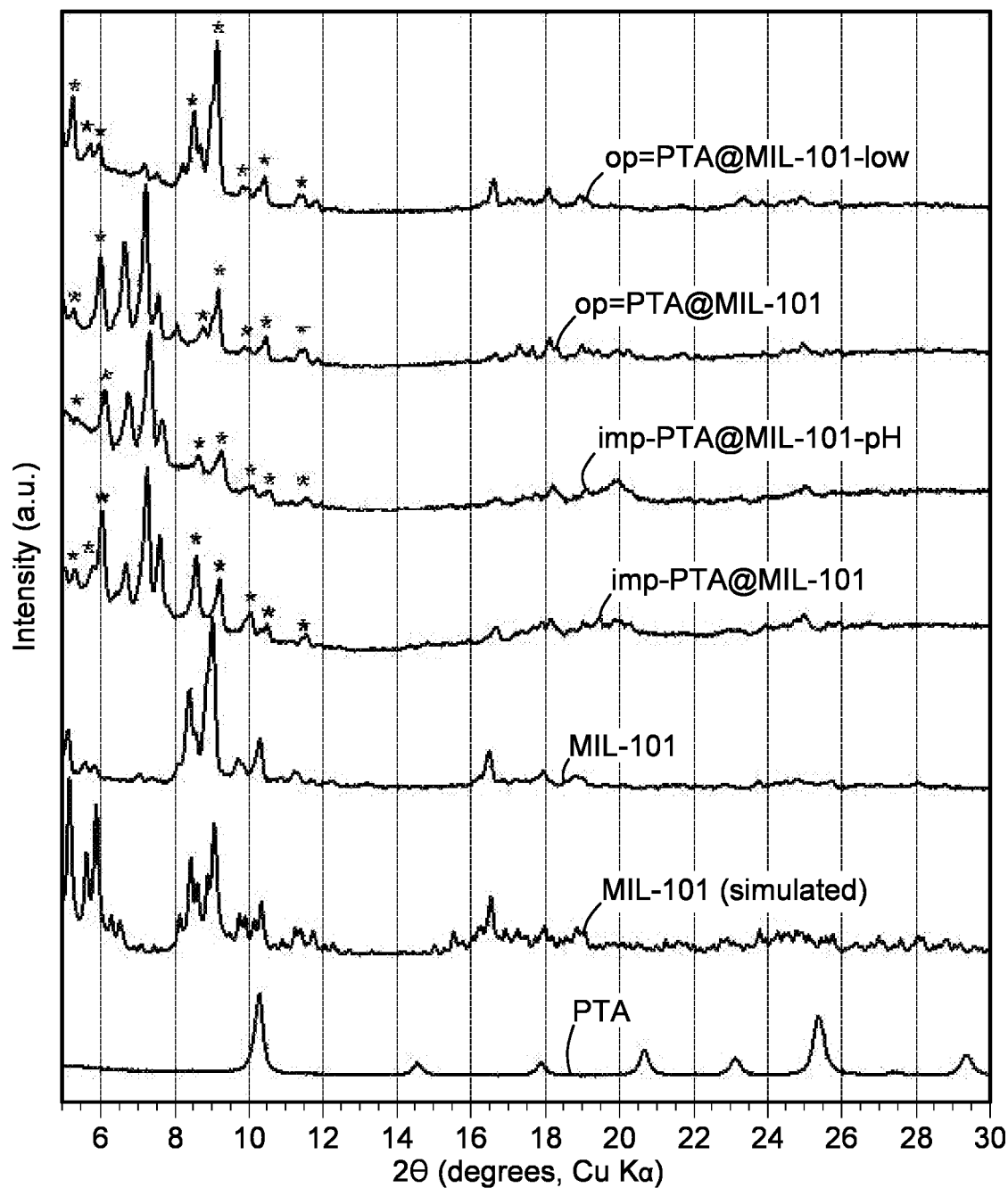
FIG. 2 depicts results from analysis of MOFs.
Figure 3:
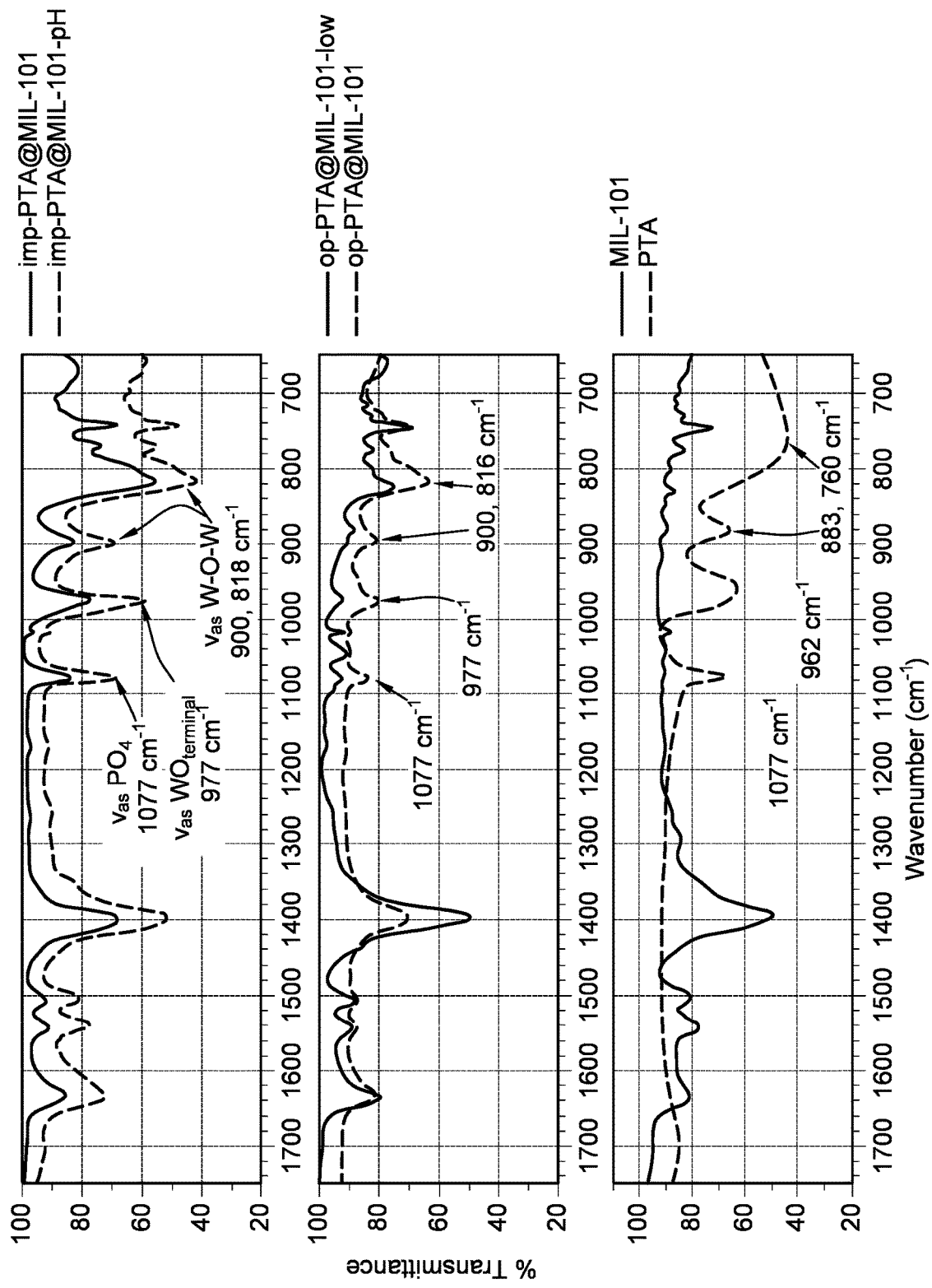
FIG. 3 depicts results from analysis of MOFs.

Different analysis such as XRD and IR spectroscopy were carried out. The XRD patterns of the MIL-101 supported PTA samples compared to pure PTA and MIL-101 are shown in FIG. 2. The IR spectroscopy of the samples are shown in FIG. 3.

Catalytic Tests for HPA Materials—Alkylation

PTA and the supported PTA samples were evaluated for both liquid-phase and supercritical-phase alkylation of isobutane and trans-2-butene. All reactions were carried out in a fixed-bed reactor. Reactor effluents were analyzed by an on-line GC using an FID detector. The samples were screened by loading the catalyst into the reactor and testing at the same activation and run temperatures, and isobutane-to-olefin of the feed. All samples were activated in situ at pre-selected temperatures under a flow of N$_2$. Bare PTA samples were also dehydrated in a furnace to remove most of the water of hydration prior to loading into the reactor. Fresh catalyst was used for each run.

Figure 4:
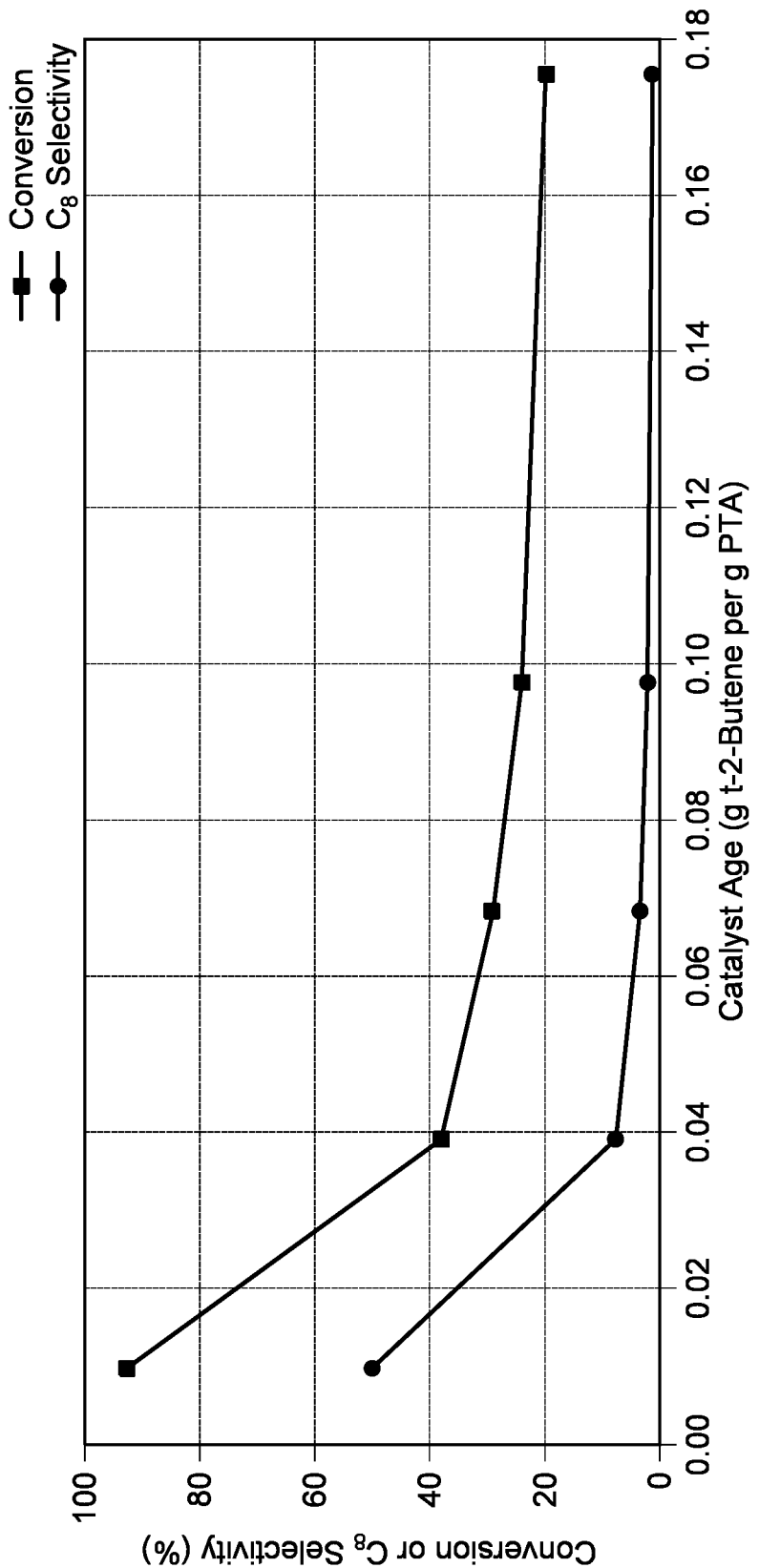
FIG. 4 depicts results from analysis of MOFs.
Figure 5A:
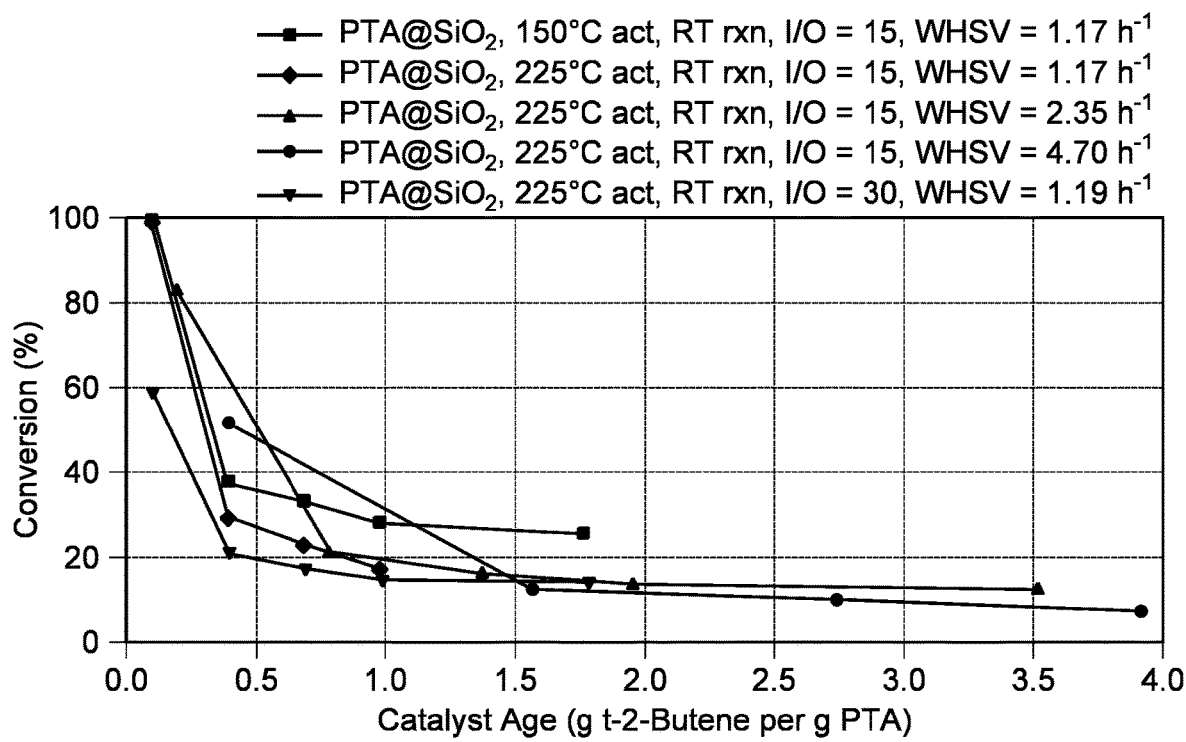
FIG. 5a depicts conversion v. catalyst age alkylation results.
Figure 5B:
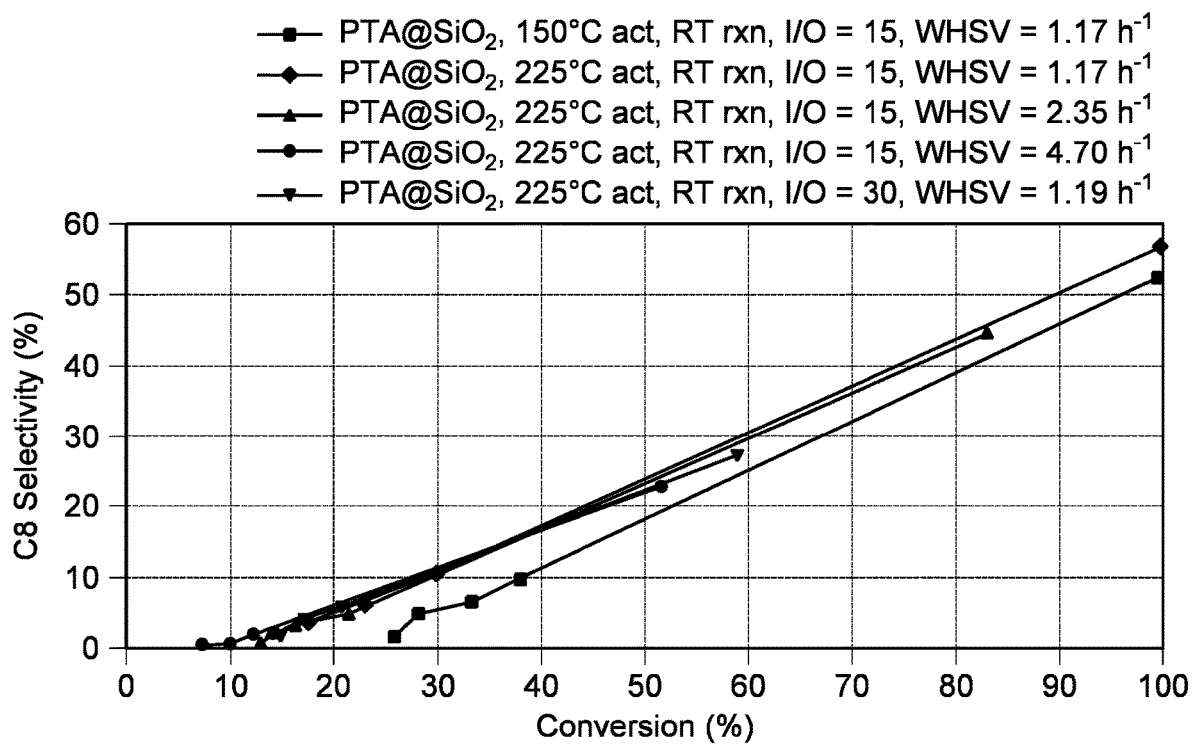
FIG. 5b depicts selectivity v. conversion results.

Results from the isobutane/trans-2-butene alkylation tests using PTA and PTA@SiO$_2$ catalysts are shown in FIG. 4 and FIGS. 5a and 5b.

FIG. 4 depicts alkylation results of showing trans-2-butene conversion and C$_8$ paraffin selectivity versus catalyst age for PTA. Test conditions for FIG. 4 were: activation temperature=225° C., reaction temperature=room temperature, isobutane-to-olefin ratio=15, WHSV=0.12 h-1.

FIG. 5a depicts conversion v. catalyst age alkylation results and FIG. 5b depicts C8 selectivity v. conversion % under different test conditions for PTA@SiO$_2$. The legend indicates the activation temperature (act), reaction temperature (rxn), isobutane-to-olefin ratio (I/O) and weight hourly space velocity (WHSV) for each test.

Figure 6A:
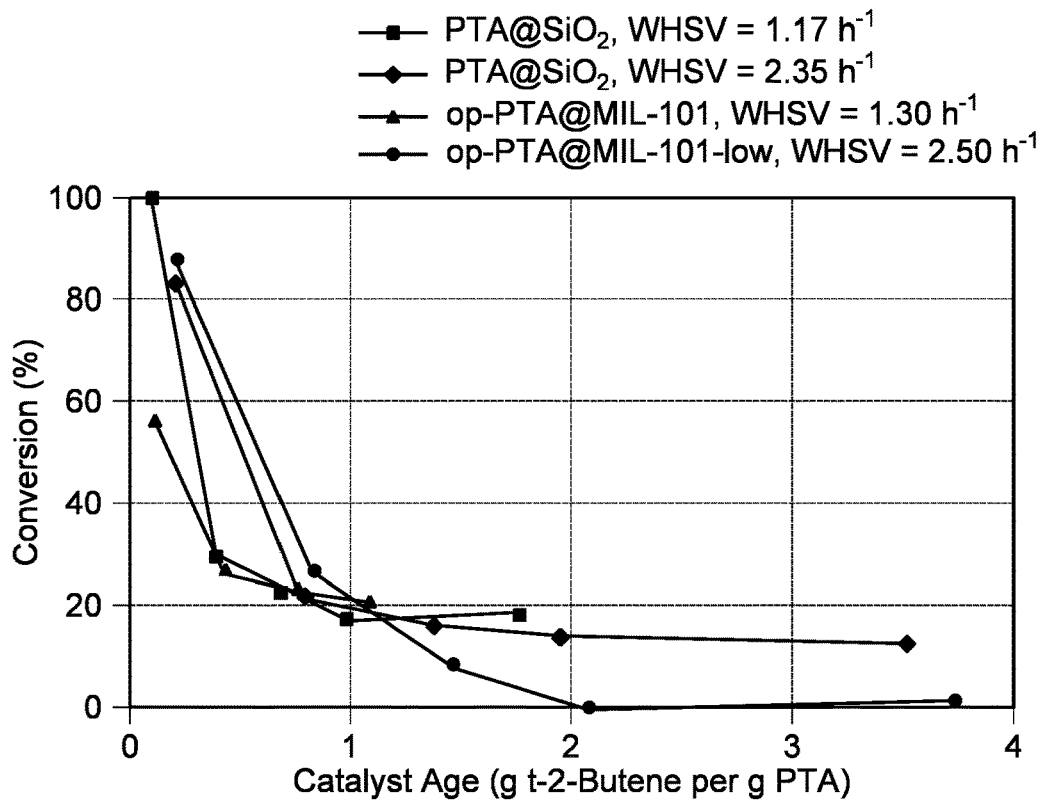
FIG. 6a depicts conversion v. catalyst age alkylation results.
Figure 6B:
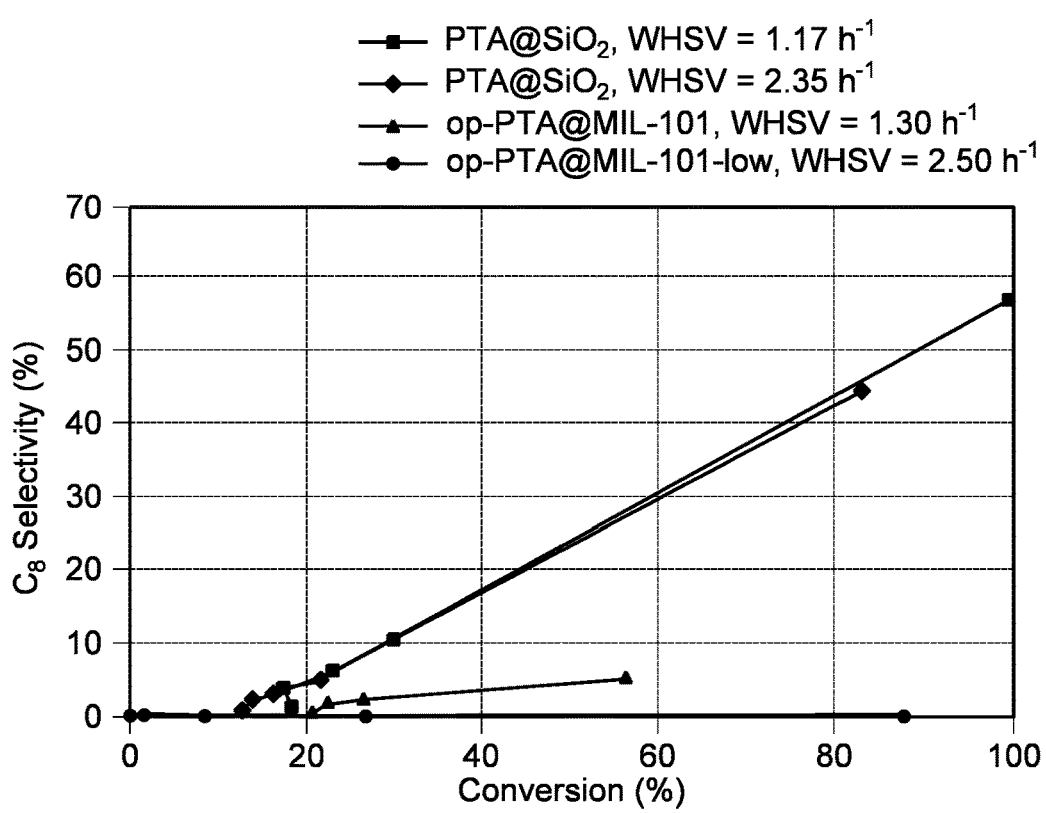
FIG. 6b depicts selectivity v. conversion results.

FIG. 6a depicts conversion v. catalyst age alkylation results and FIG. 6b depicts C8 selectivity v. conversion % for op-PTA@MIL-101 samples with results for PTA@SiO$_2$ tested under similar WHSV are included for comparison. Test conditions for FIG. 6a and FIG. 6b were: activation temperature=225° C., reaction temperature=room temperature, reaction pressure=300 psi and isobutane-to-olefin I/O=15.

Figure 7A:
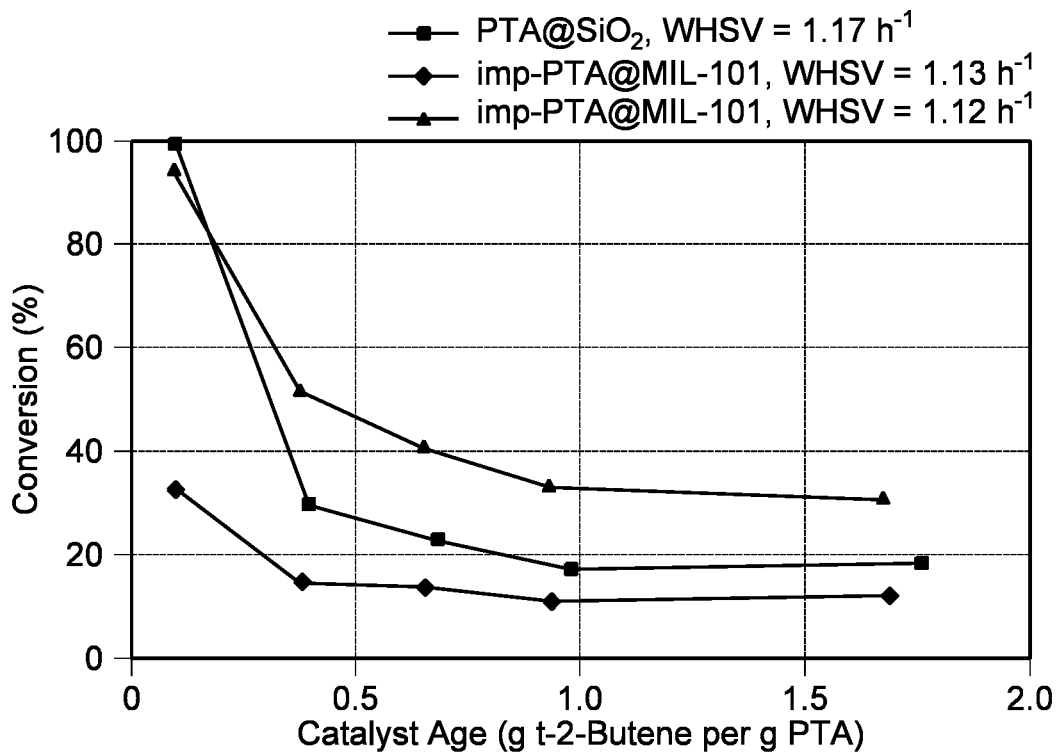
FIG. 7a depicts conversion v. catalyst age alkylation results.
Figure 7B:
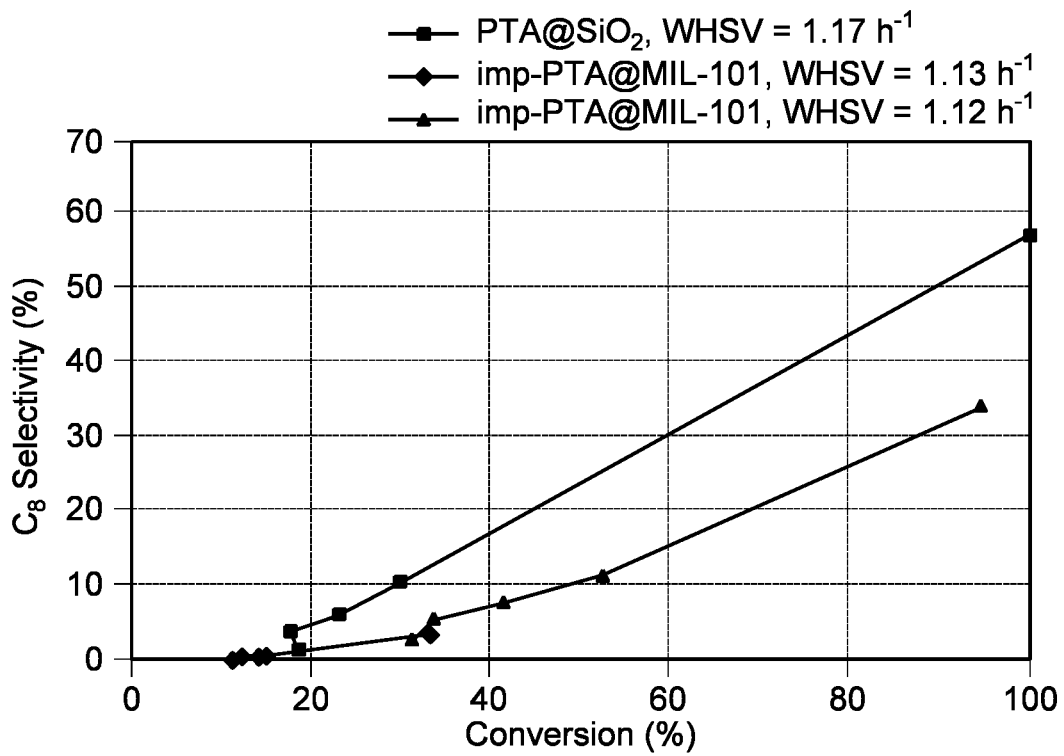
FIG. 7b depicts selectivity v. conversion results.

FIG. 7a depicts conversion v. catalyst age alkylation results and FIG. 7b depicts C8 selectivity v. conversion % depicts alkylation results for imp-PTA@MIL-101 samples with results for PTA@SiO$_2$ tested under similar WHSV are included for comparison. Test conditions for FIG. 7a and FIG. 7b were: activation temperature=225° C., reaction temperature=room temperature, reaction pressure=300 psi and isobutane-to-olefin I/O=15.

Figure 8A:
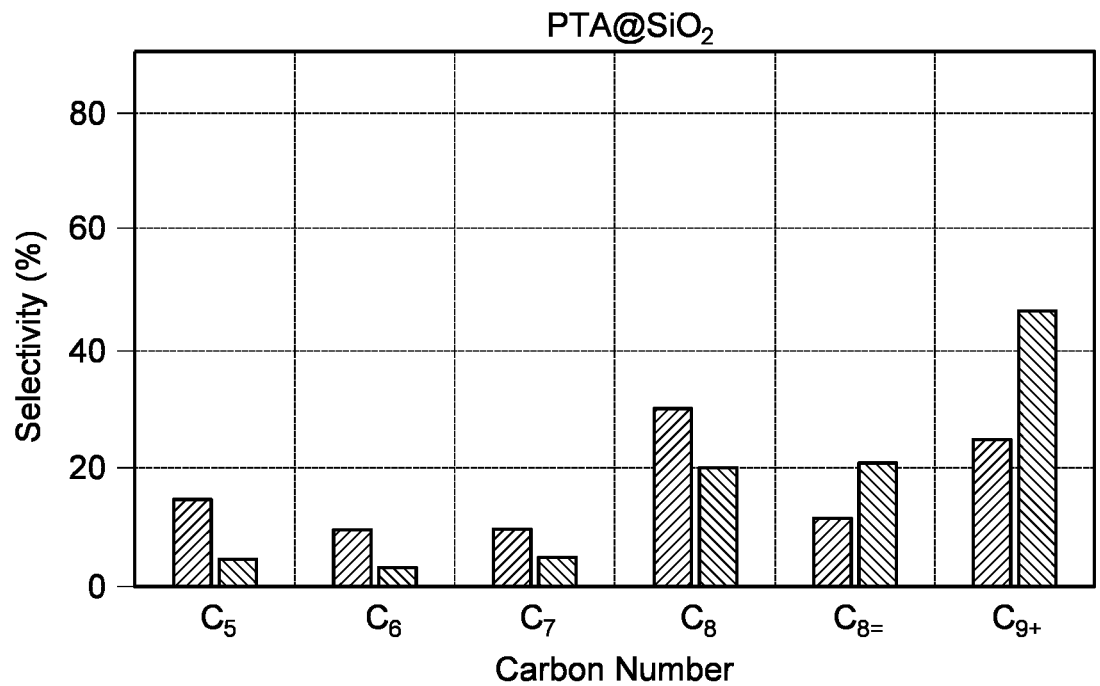
FIG. 8a depicts supercritical alkylation results.
Figure 8B:
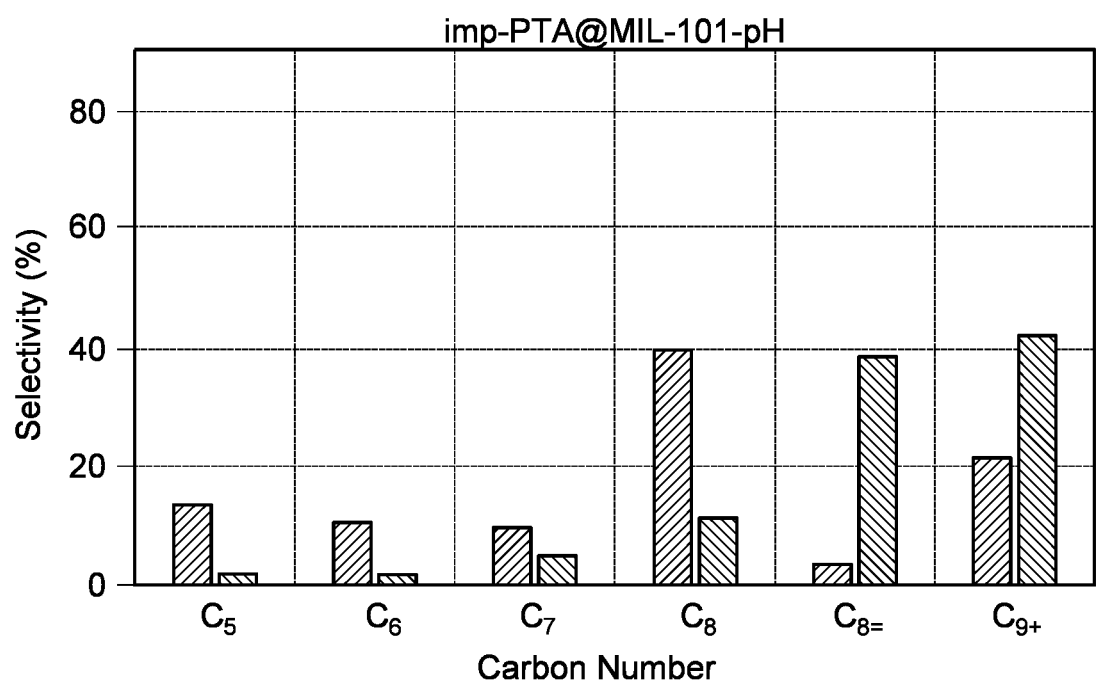
FIG. 8b depicts supercritical alkylation results.

FIG. 8a and FIG. 8b depicts the supercritical alkylation using PTA@SiO$_2$ and imp-PTA@MIL-101-pH as catalyst. Test conditions for FIG. 8a and FIG. 8b were: activation temperature=225° C., reaction temperature=137° C., reaction pressure=653 psig and isobutane-to-olefin I/O=33.25.

Figure 9:
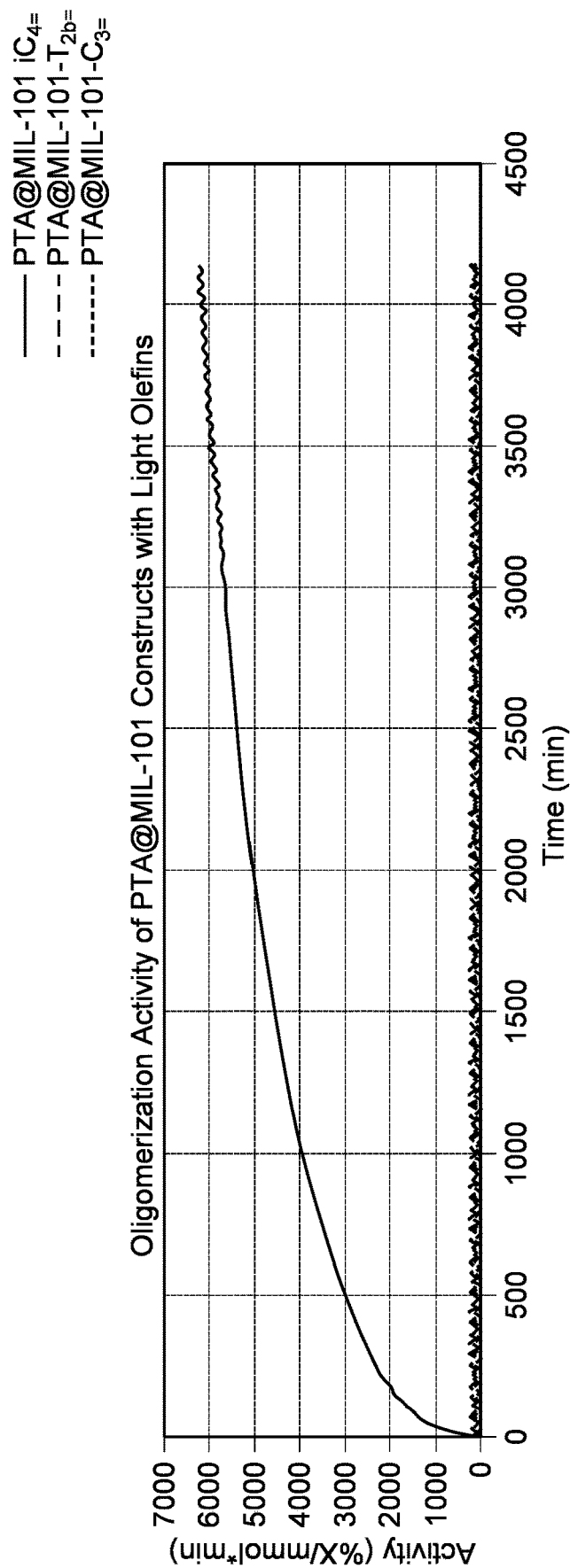
FIG. 9 depicts activation results.

FIG. 9 depicts the activity in a batch reactor for imp-PTA@MIL-101 for the oligomerization of isobutene, trans-2-butene and propylene in terms of conversion versus time.

Figure 10:
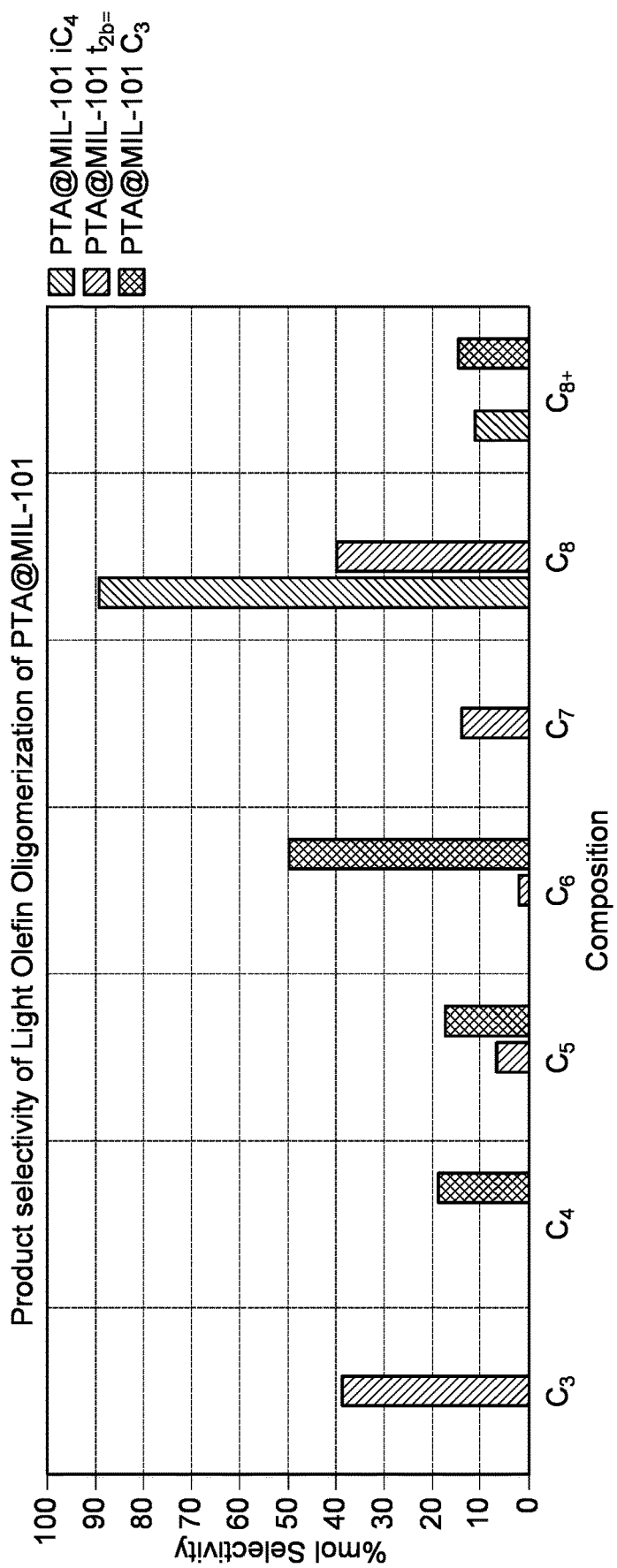
FIG. 10 depicts selectivity results.

FIG. 10 depicts the product selectivity of imp-PTA@MIL-101 for the oligomerization of isobutene, trans-2-butene and propylene in a batch reactor.

Example 3

Sulfonic Acid-Functionalized MOFs

Catalysts bearing perfluorinated sulfonic acid groups have high acid strength. A well-known example is Nafion, which had been reported in literature as an alkylation catalyst. In this invention, solid acid catalysts comprised of MOFs bearing halogenated and non-halogenated alkyl- and arylsulfonic acid sites are targeted.

The solid acid catalysts disclosed in this example are MOFs functionalized with halogenated and non-halogenated alkyl and aryl sulfonic acids. The functionalized MOF is prepared by a reaction between the nucleophilic groups present in the MOF's building units and cyclic sulfonate esters called sultones. Such reaction can yield sulfonic acids in the MOF's internal surface. These MOFs may be used as acid catalysts, even for those reactions that require high acid strength such as isoparaffin-olefin alkylations. Using per-flourinated sultones can yield perfluorosulfonic acid sites on the MOFs, reminiscent of the highly acidic sites found in Nafion, and thus yielding an acid MOF catalyst that is a suitable candidate for alkylation catalysis.

Figure 11:
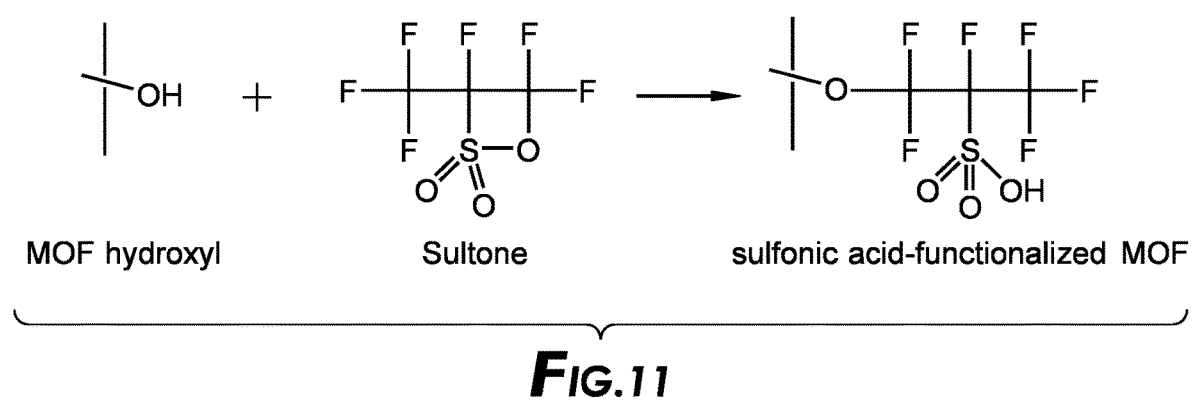
FIG. 11 depicts a reaction scheme.
Figure 12:
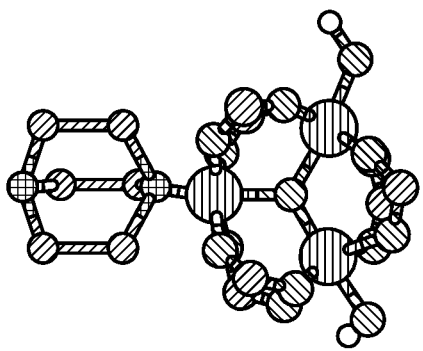
FIG. 12 depicts example MOF building units.
Figure 12:
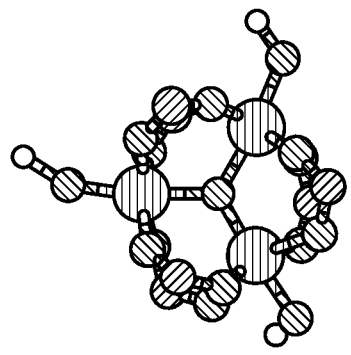
Figure 12:
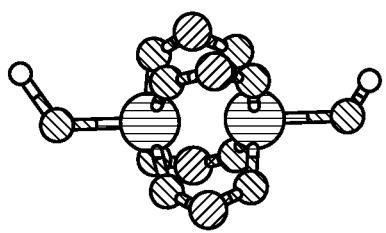
Figure 12:
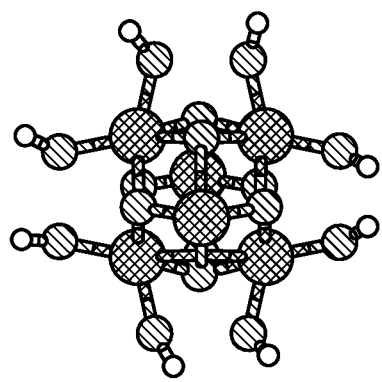
Figure 13:
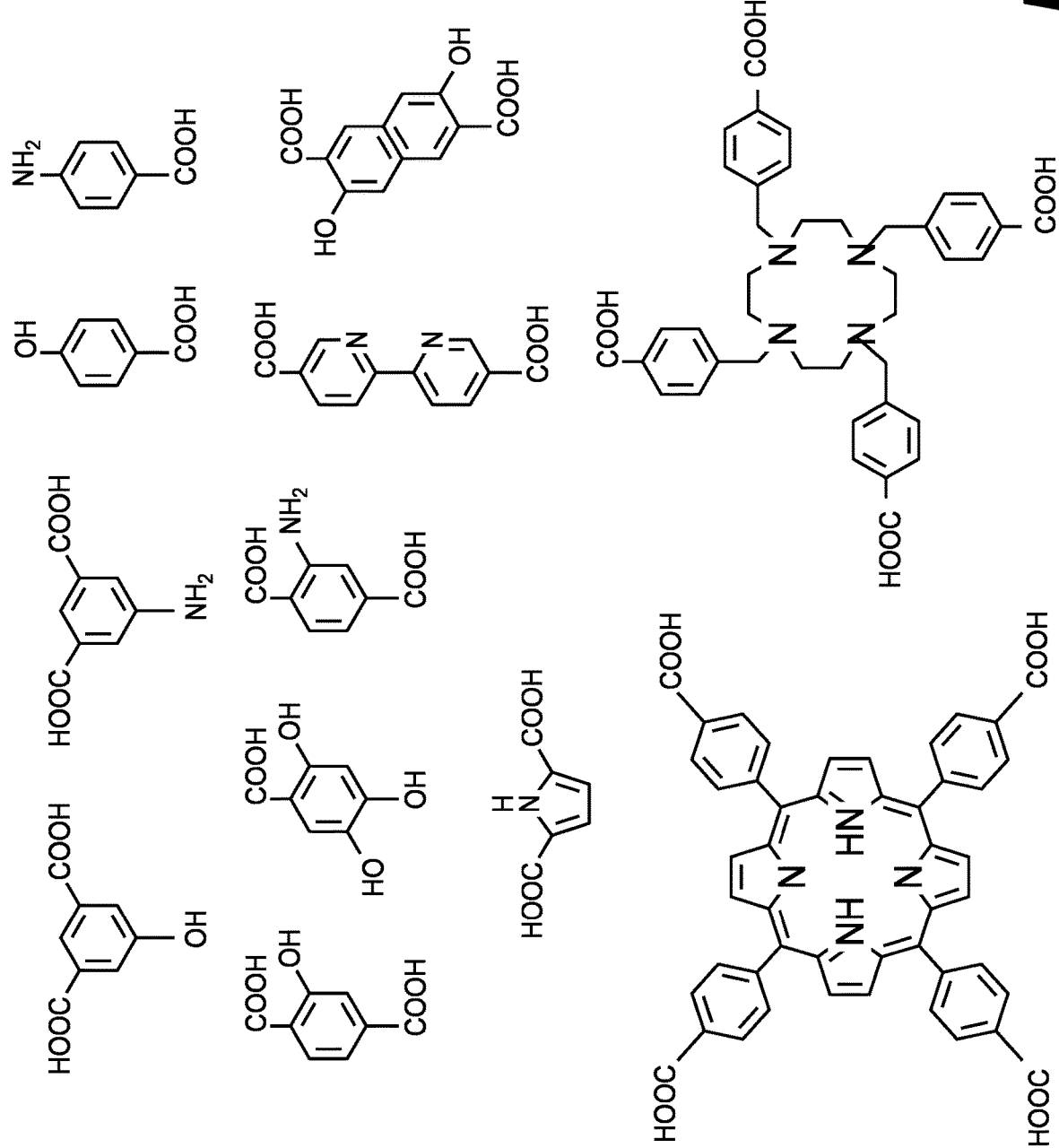
FIG. 13 depicts example MOF ligands.

FIG. 11 shows the reaction scheme for the condensation between a MOF hydroxyl and a sultone. FIG. 12 shows examples of MOF building units bearing such nucleophilic functionalities such as amino- and hydroxyl groups. FIG. 13 shows examples of MOF ligands bearing such nucleophile functionalities such as amino and hydroxyl groups.

Figure 14:
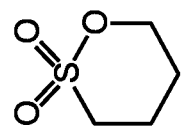
FIG. 14 depicts non-limiting representative sultones.
Figure 14:
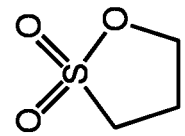
Figure 14:
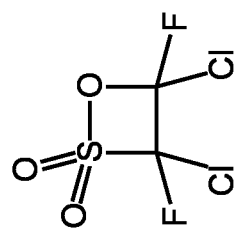
Figure 14:
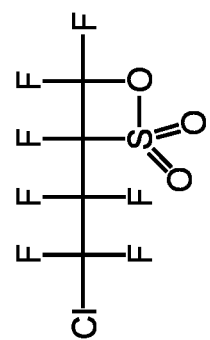
Figure 14:
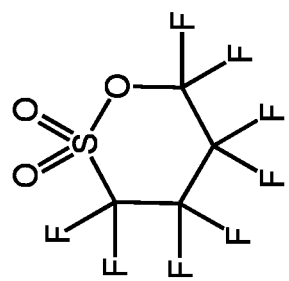
Figure 14:
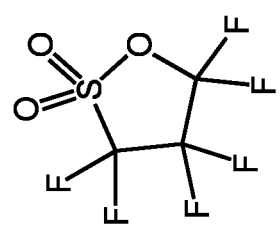
Figure 14:
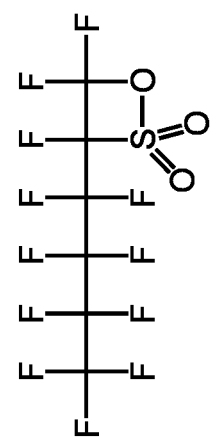
Figure 14:
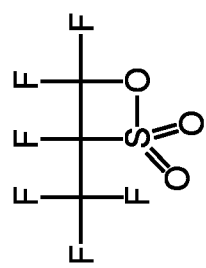

Sultones that can be used for this synthesis include, but are not limited to, the examples shown in FIG. 14.

In one embodiment, the solid metal-organic framework composition can comprise a solid metal-organic framework supported sulfonic acid wherein the sulfur content is greater than 0.5 mmol/gram. The composition of solid metal organic framework supported sulfonic acid can be made by reacting the metal organic framework with sultones in solution at temperatures ranging from 25° C. to 200° C. to form the sulfonic acid-functionalized metal organic framework. The functionalized metal organic framework is dried to obtain the solid metal organic framework supported sulfonic acid. In one embodiment the reaction of the metal organic framework with the sultone occurs without any external applied heat.

Alternatively, perfluorinated sulfonic acid sites can be generated in MOFs using multifunctional organic molecules, where one functionality is the perfluorinated sulfonic acid group and the other is a binding motif for the metal organic framework such as, but not limited to, a carboxylate or another sulfonic acid group.

The process of a reaction can be a heterogenous reaction between a solid metal organic framework supported sulfonic acid and a hydrocarbon feed. This modified hydrocarbon stream can comprise essentially of $C_{6+}$ hydrocarbons.

Preparation of Sulfonic Acid-Functionalized MOFs

MOF-808. MOF-808 was synthesized by dissolving $ZrOCl_2 \cdot 8H_2O$ in formic acid. 1,3,5-benzenetricarboxylic acid was also dissolved in anhydrous DMF to create a separate solution. The two solutions were mixed, allowed to react under suitable conditions to form the MOF, and the solids were extracted. The solids were then treated with HCl. Finally, the solids were washed, air-dried and then heat-treated.

Hf-MOF-808. Hf-MOF-808 was prepared in the same manner as MOF-808, except using $HfCl_4$ instead of $ZrOCl_2 \cdot 8H_2O$ as metal precursor for the synthesis.

MIL-101. MIL-101 was synthesized by dissolving $Cr(NO_3)_3 \cdot 9H_2O$ in an aqueous solution of $HNO_3$. Terephthalic acid was then added and reacted in a heated reactor. The product was then extracted and heat treated.

Sulfonic Acid Functionalization of MOF Supports. Sulfonic acid sites were incorporated in MOFs by refluxing the MOFs in a toluene solution of the desired sultone under inert atmosphere. After the reaction mixture is cooled down to room temperature, the solids were washed and dried to obtain the solid sulfonic acid-functionalized MOFs.

Properties:

Both MOF and silica supports were functionalized with sulfonic acids to demonstrate the different sulfur content in the sultone grafted product. Table 3 depicts the results

TABLE 3

| Support | Sultone | Sample Name | Sulfonic acid to MOF Node Ratio in MOF Product | S content in grafted product (mmol/g) |
|---|---|---|---|---|
| MOF-808 | 1,4-butane sultone | $C_4H_8SO_3H$@MOF-808 | 3.6 | 2.09 |
| MIL-101 | | $C_4H_8SO_3H$@MIL-101 | 1.1 | 1.47 |
| MOF-808 | hexafluoro(3-methyl-1,2-oxathietane)-2,2-dioxide | $C_3F_6SO_3H$@MOF-808 | 2.3 | 1.85 |
| Hf-MOF-808 | | $C_3F_6SO_3H$@Hf-MOF-808 | 1.7 | 0.83 |
| Commercial Silica Sample A | | $C_3F_6SO_3H$@SBA-15 | N/A | 0.17 |
| Commercial Silica Sample B | | $C_3F_6SO_3H$@MCM-41 | N/A | 0.28 |
| MOF-808 | 1-(nonafluorobutyl) trifluoroethane sultone | $C_6F_{12}SO_3H$@MOF-808 | 1.2 | 1.07 |

Catalytic Tests for Sulfonic Acid-Functionalized MOFs—Alkylation

Samples were evaluated for both liquid-phase and supercritical-phase alkylation of isobutane and trans-2-butene. All reactions were carried out in a fixed-bed reactor. Reactor effluents were analyzed by an on-line GC using an FID detector. The samples were screened by loading the catalyst into the reactor and testing at the same activation and run temperatures, and isobutane-to-olefin of the feed. All samples were activated in situ at pre-selected temperatures under a flow of $N_2$. Fresh catalyst was used for each run.

Two methods were used to for the regeneration of the partially deactivated catalyst bed. One is by heating under $N_2$. The second method was supercritical isobutane regeneration at temperatures and pressures above the supercritical point for isobutane.

Figure 15:
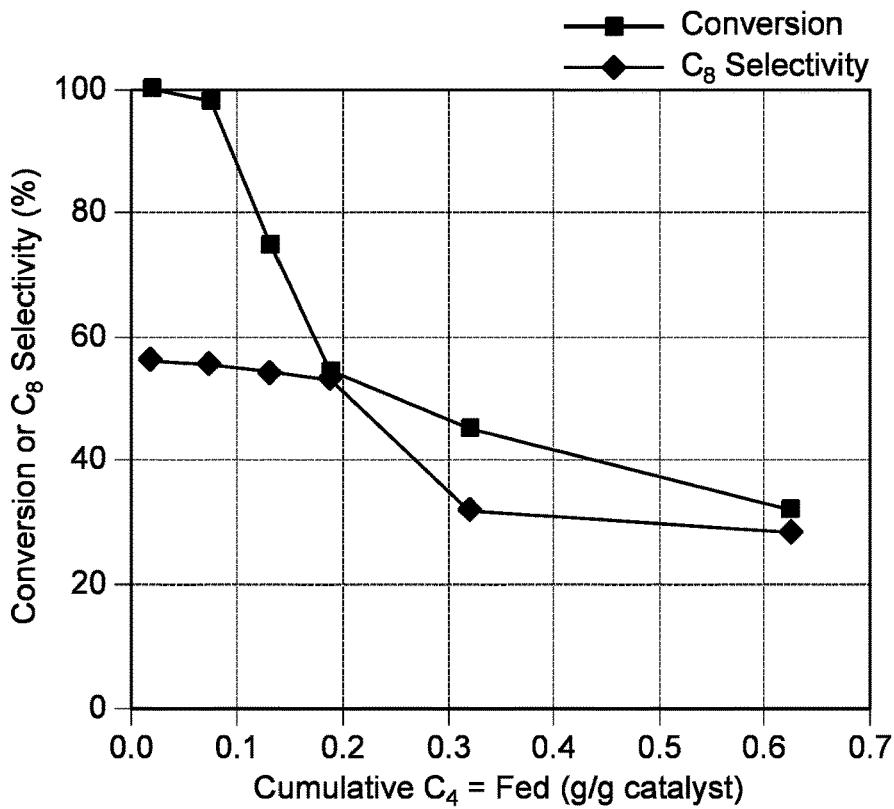
FIG. 15 depicts alkylation results.
Figure 16:
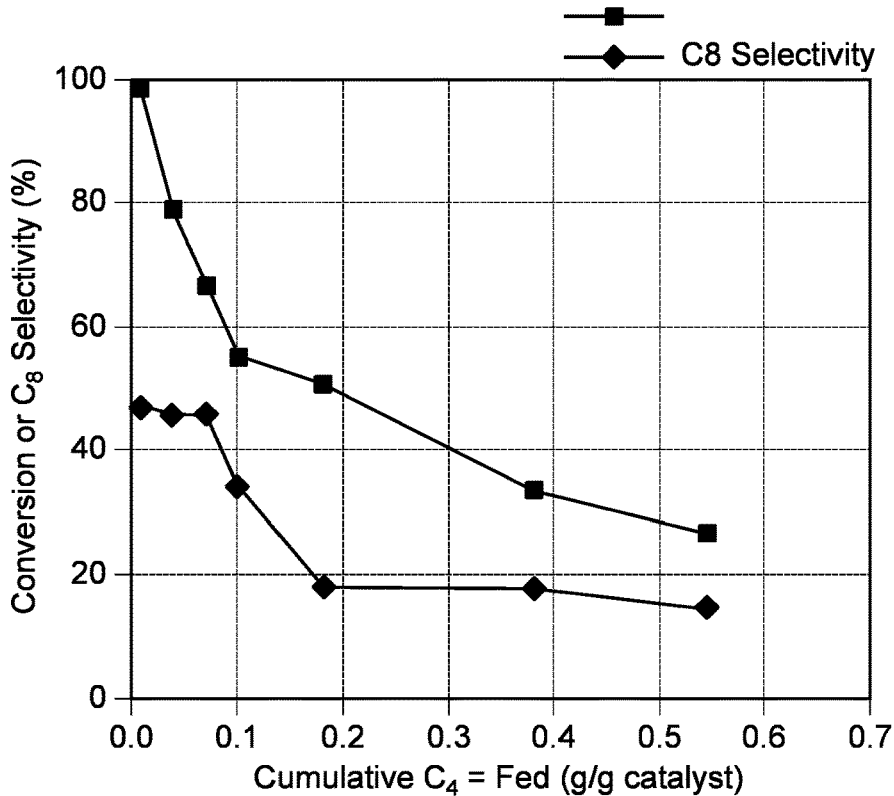
FIG. 16 depicts alkylation results.
Figure 17:
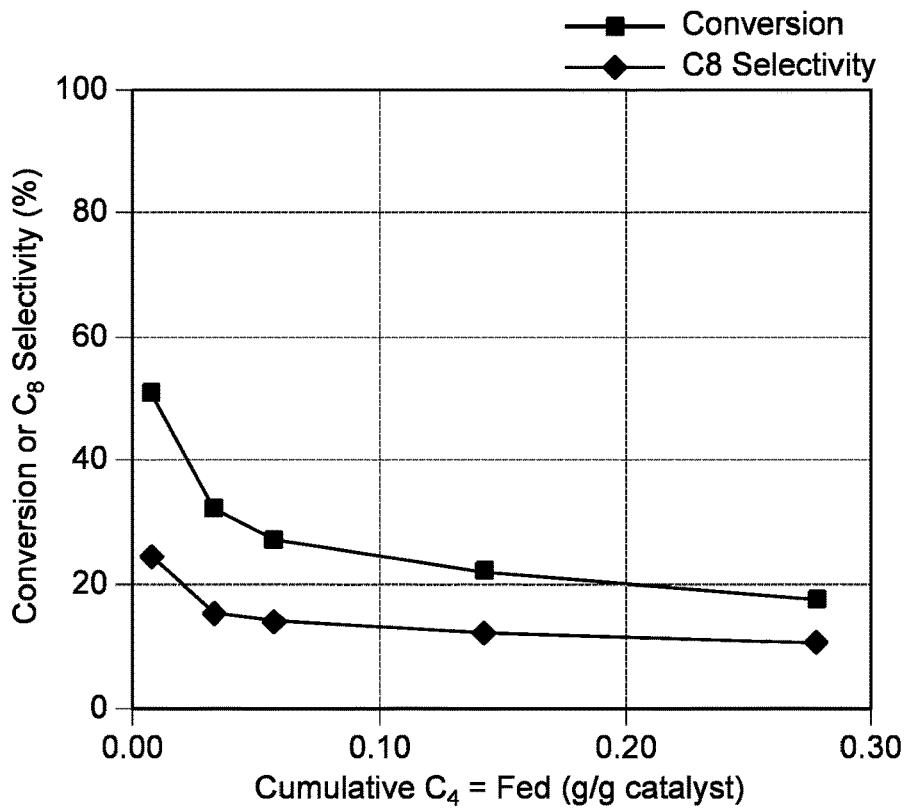
FIG. 17 depicts alkylation results.

FIG. 15, FIG. 16, and FIG. 17 depict the liquid-phase alkylation of isobutane with trans-2-butene using different sulfonic acid-decorated MOF catalysts.

FIG. 15 depicts alkylation results for $C_3F_6SO_3H$@MOF-808 catalyst samples. Test conditions for FIG. 15 were: reaction temperature=80° C., reaction pressure=300 psi and isobutane-to-trans-2-butene ratio I/O=134, and weight hourly space velocity of 0.12 $h^{-1}$. The sulfonic acid to MOF node ratio in the product was 1.5 with a S content in the sultone grated product of 1.97 mmol/g.

FIG. 16 depicts alkylation results for $C_6F_{12}SO_3H$@MOF-808 catalyst samples. Test conditions for FIG. 16 were: reaction temperature=80° C., reaction pressure=300 psi and isobutane-to-trans-2-butene ratio I/O=134, and weight hourly space velocity of 0.12 $h^{-1}$. The sultone to MOF node ratio in the product was 1.2 with a S content in the sultone grated product of 1.07 mmol/g.

FIG. 17 depicts alkylation results for $C_3F_6SO_3H$@Hf-MOF-808 catalyst samples. Test conditions for FIG. 17 were: reaction temperature=80° C., reaction pressure=300 psi and isobutane-to-trans-2-butene ratio I/O=128, and weight hourly space velocity of 0.10 $h^{-1}$. The sulfonic acid to MOF node ratio in the product was 1.7 with a S content in the sultone grated product of 0.83 mmol/g.

Figure 18:
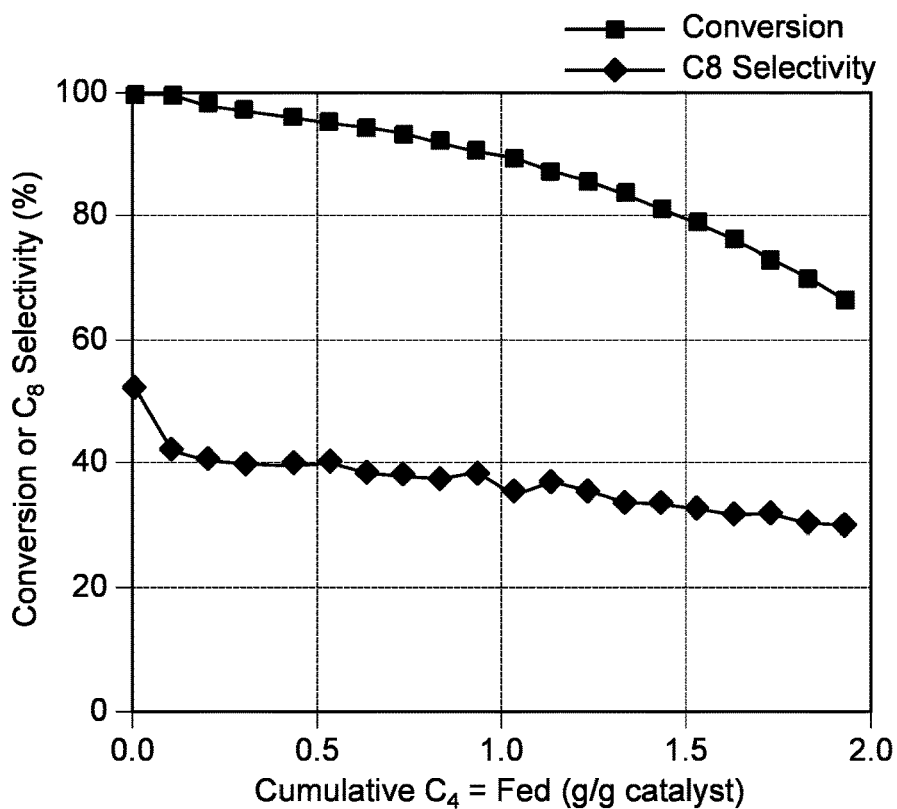
FIG. 18 depicts supercritical alkylation results.

FIG. 18 depicts the supercritical alkylation of isobutane and trans-2-butene with a sulfonic acid-decorated MOF ($C_3F_6SO_3H@MOF$-808). Test conditions for FIG. 18 were: reaction temperature=137° C., reaction pressure=635 psi and isobutane-to-trans-2-butene ratio I/O=134, and weight hourly space velocity of 0.07 $h^{-1}$. The sultone to MOF node ratio in the product was 2.34 with a S content in the sultone grated product of 1.85 mmol/g.

Figure 19:
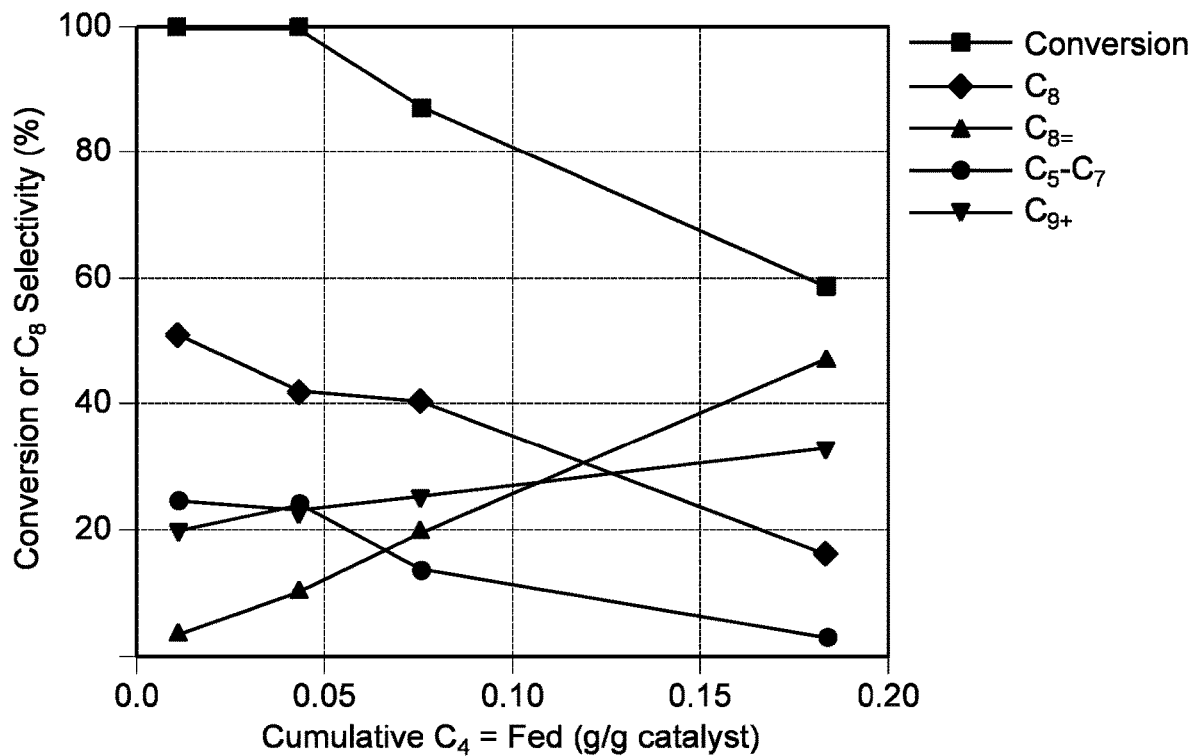
FIG. 19 depicts the alkylation results.

FIG. 19 depicts the alkylation results for $C_3F_6SO_3H@MOF$-808 catalyst samples. Test results for FIG. 19 were: reaction temperature=80° C., reaction pressure=300 psi and isobutane-to-olefin ratio I/O=76, and weight hourly space velocity of 0.13 $h^{-1}$.

Figure 20:
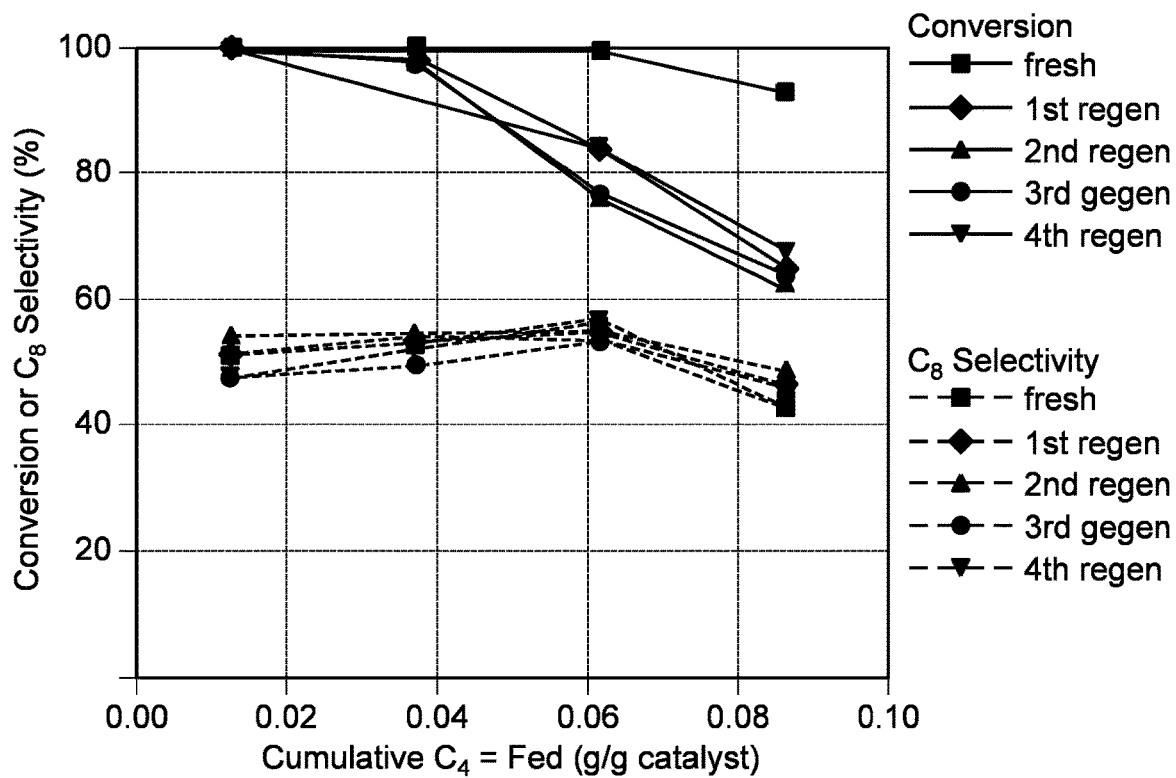
FIG. 20 depicts the alkylation results.

FIG. 20 depicts alkylation results for $C_3F_6SO_3H@MOF$-808 catalyst with supercritical isobutane regeneration. In supercritical isobutane regeneration the feed is switched from the reaction mixture to pure isobutane to stop the alkylation step. After flushing with isobutane for 30 min, the reactor temperature was increased to 137° C. and the pressure to 653 psi. Supercritical isobutane regeneration was carried out for 4 h at a WHSV of 33 $h^{-1}$. After the regeneration step was completed, the reactor is brought back to the reaction temperature and pressure, and the flow of the reaction mixture was started for the next alkylation step. Test results for FIG. 20 were: reaction temperature=80° C., reaction pressure=300 psi and isobutane-to-olefin ratio I/O=134, and weight hourly space velocity of 33 $h^{-1}$.

Figure 21:
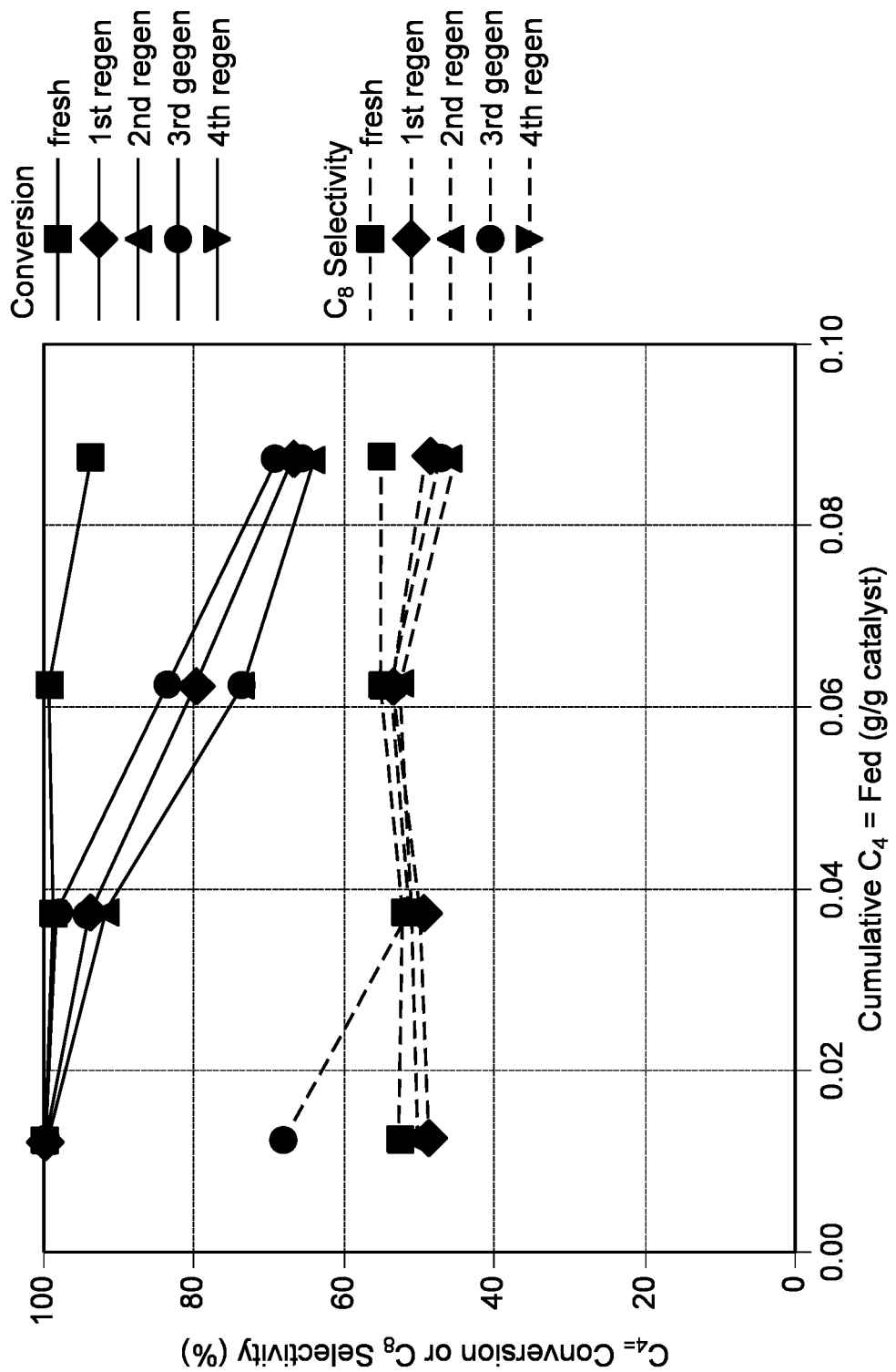
FIG. 21 depicts the alkylation results.

FIG. 21 depicts alkylation results for $C_3F_6SO_3H@MOF$-808 catalyst with regeneration under $N_2$ flow. In regeneration under $N_2$ flow after stopping the reaction mixture flow, the reactor is flushed for 30 min with a 50 mL/min flow of $N_2$. The reactor temperature was then increased to 110° C. and the pressure dropped to atmospheric. After 12 h of regeneration, the reactor is brought back to the reaction temperature and pressure, filled throughout with isobutane and the flow of the reaction mixture was started for the next alkylation step. FIG. 21 were: reaction temperature=80° C., reaction pressure=300 psi and isobutane-to-olefin ratio I/O=134, and weight hourly space velocity of 0.15 $h^{-1}$.

The product distribution from the alkylation of isobutane with trans-2-butene catalyzed by a perfluorinated sulfonic acid-functionalized MOF ($C_3F_6SO_3H@MOF$-808) is shown in Table 4. Reaction conditions: temperature=80° C., pressure=300 psi, and weight hourly space velocity (WHSV)= 0.13 $h^{-1}$. The production of $C_8$ paraffins indicates that this acid MOF is capable of catalyzing the alkylation reaction of isobutane with trans-2-butene. TMP is trimethylpentane, and DMH is dimethylhexane.

TABLE 4

| TOS (min) | 35 |
|---|---|
| Olefin Conversion (%) | 87 |
| $C_{5+}$ product distribution (%) | |
| $C_5$-$C_7$ | 14 |
| $C_8$ | 41 |
| $C_{8-}$ | 20 |
| $C_{9+}$ | 25 |
| $C_8$ product distribution (%) | |
| 2,2,4-TMP | 11 |
| 2,2,3-TMP | 1 |
| 2,3,4-TMP | 20 |
| 2,3,3-TMP | 12 |
| DMHs | 56 |

Catalytic Tests for Sulfonic Acid-Functionalized MOFs—Oligomerization

Oligomerization catalytic testing was performed in a pressurized batch reactor. The catalyst was pre-treated using vacuum and heat. Then the reactor was pressurized with the desired olefin. The pressure and temperature were monitored and was used to calculate conversion. At the end of the run a gas sample was collected and analyzed by gas chromatography to determine the product distribution.

We describe of using sulfonic acid functionalized-MOF-808 to oligomerize isobutane ($iC_4$), propylene ($C_3$), and trans-2-butylene(t2b). The activity is compared to MOF-808 $SO_4$.

Figure 22:
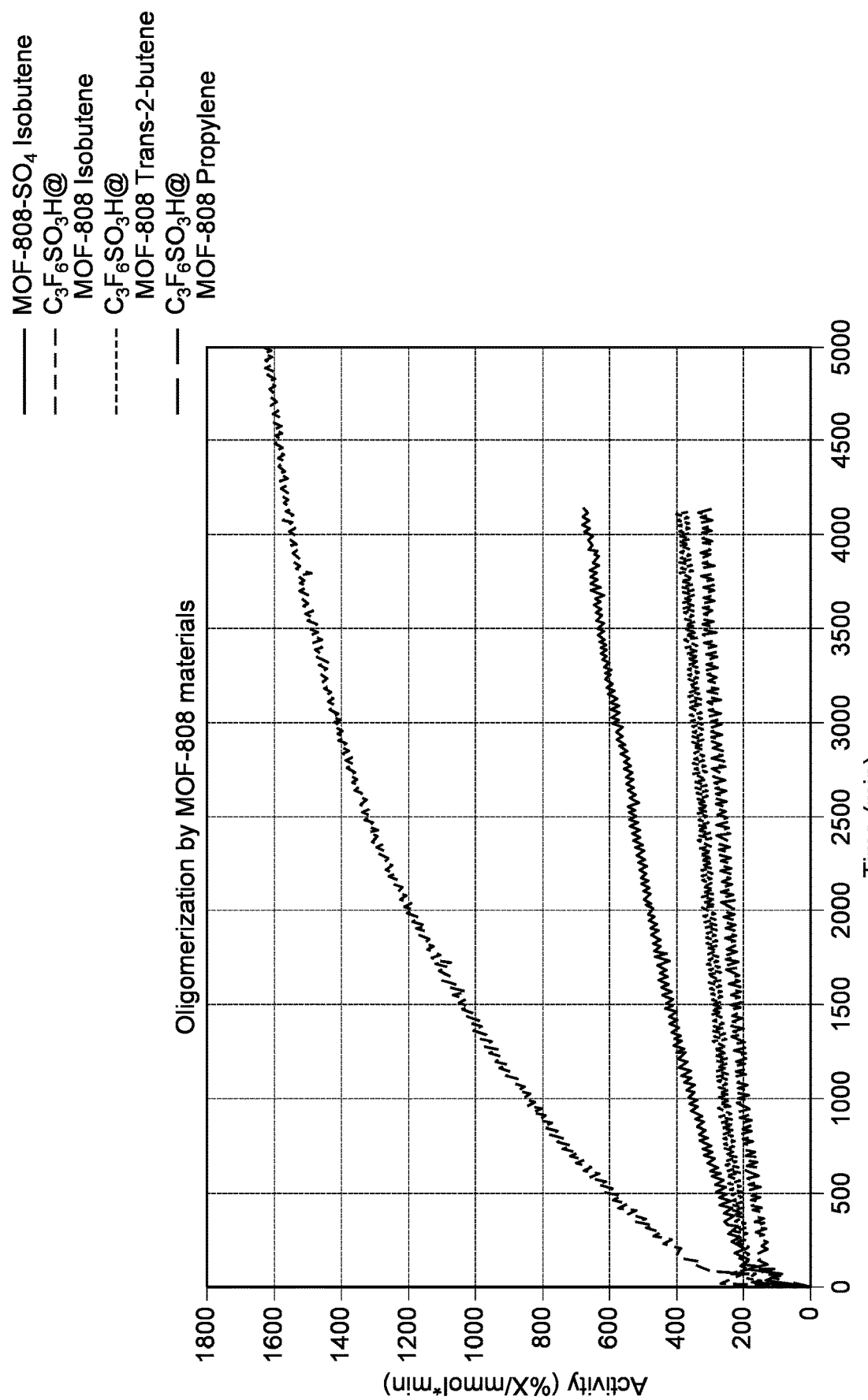
FIG. 22 depicts the oligomerization results.

FIG. 22 depicts the results of the oligomerization reaction over the various sulfonic acid-functionalized MOF-808 materials over time. MOF-808-$SO_4$, described in the next Example, was included in the plot as a reference.

Figure 23:
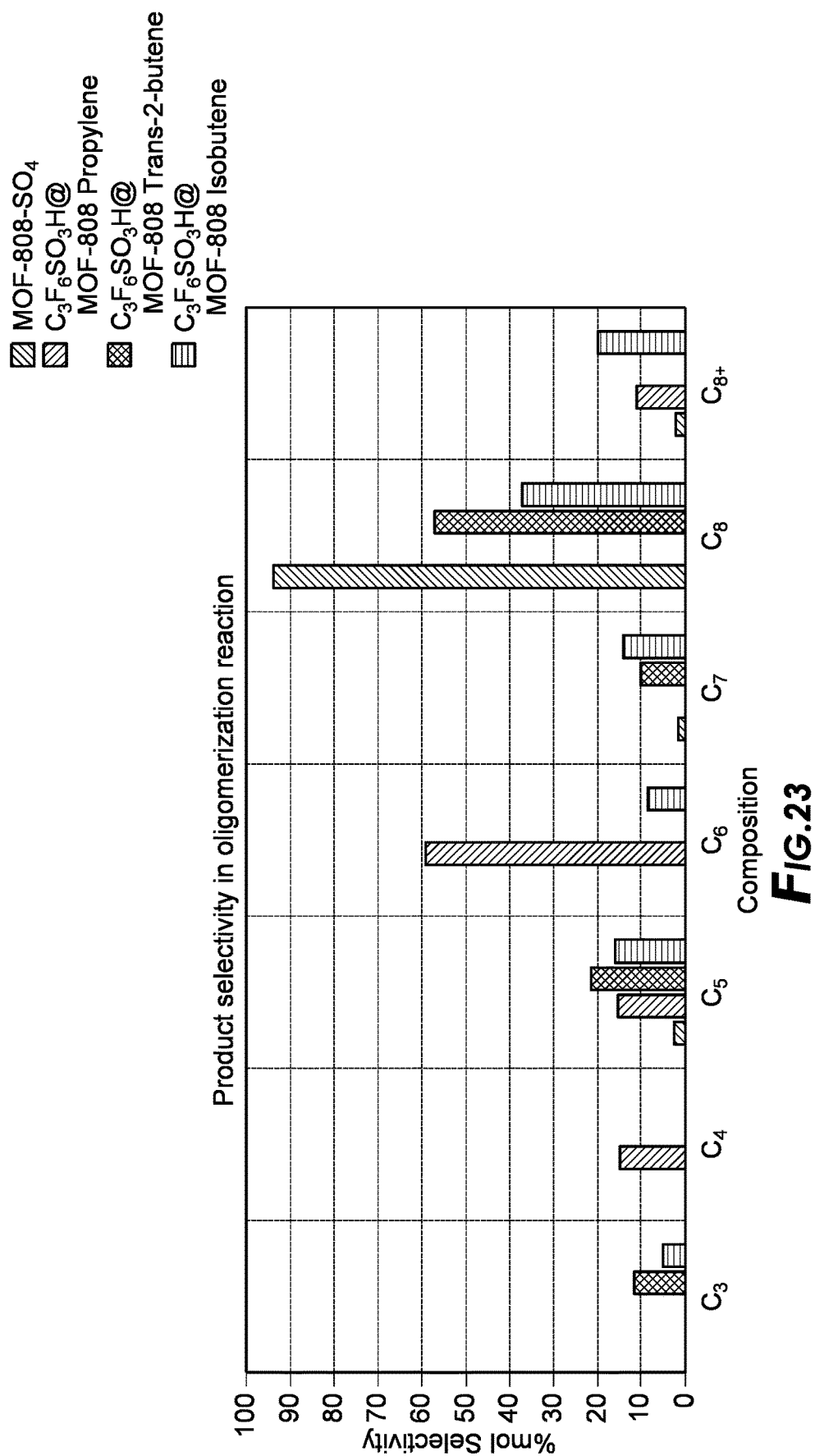
FIG. 23 depicts the product selection results.

FIG. 23 depicts the product selectivity for the oligomerization reaction over the various sulfonic acid-functionalized MOF-808 materials over time. MOF-808-$SO_4$, described in the next Example, was included in the plot as a reference.

Example 4

Oxyanion-Modified Metal Organic Frameworks

In one example a superacidic MOF can be sulfated into MOF-808. This MOF analogue of sulfated zirconia (SZ) is prepared by immersing MOF-808 in dilute $H_2SO_4$, resulting in adsorbed sulfates on the MOF's zirconium oxocluster node. The sulfated node (~0.5 nm in size) can be considered a nano-sized SZ.

In this example we describe a process that uses an acidic MOF that can selectively oligomerize light olefins ($C_3$-$C_6$) to more valuable, heavier products (high octane gasoline, low sulfur diesel, jet fuel, specialty solvents or synthetic lube oils) which have been forecast to have great growth potential despite the forecasted changes in gasoline demand. As an example of how this process might be applied a MOF capable of reacting only with isobutene can be used to upgrade a mixed $C_4$ olefin feed into to a more valuable $C_{12}$ and $C_8$ olefin stream.

MOFs can also be made with different metals as nodes and different acid site functionalities. As described above the metal ion nodes could be composed of one or more metal ions from Group 1 through 16 of the IUPAC Periodic Table of the Elements including actinides, and lanthanides, and combinations thereof.

The loading of the metals on the nodes can be 1 atom per node, 2 atoms per node, 3 atoms per node, 4 atoms per node, 5 atoms per node, 6 atoms per node, 7 atoms per node, or even 8 atoms per node or more. In one non-limiting example oxygen can be loaded onto the solid metal organic framework from 1 atom per node, 10 atoms per node, 20 atoms per node, or even 25 atoms per node and greater.

The composition of an oxyanion-modified metal organic framework can be made by mixing a previously prepared solid metal-organic framework and a solution of suitable concentration of the desired oxyanion in either aqueous or organic media. The resulting suspension is allowed to react and equilibrate over a suitable period of time. The solid can then be then recovered, washed and dried to form an oxyanion-modified metal organic framework.

The process of a reaction can be a heterogenous reaction between a solid oxyanion-modified metal organic framework and a hydrocarbon feed. This modified hydrocarbon stream can comprise essentially of $C_{6+}$ hydrocarbons.

Oxyanion-Modified Metal Organic Frameworks Examples:

Zr-MOF-808 Base material. A solution of zirconium oxychloride and formic acid in DMF was combined with a solution of BTC linker in DMF. The solution was placed in an oven and heated to a suitable temperature for the formation of the MOF structure. The MOF precipitate was collected by centrifugation and washed with of fresh solvent and heat treated to yield activated sample.

Hf-MOF-808 Base material. A solution of hafnium oxychloride and formic acid in DMF was combined with a solution of BTC linker in DMF. The solution was placed in an oven and heated to a suitable temperature for the formation of the MOF structure. The MOF precipitate was collected by centrifugation and washed with of fresh solvent and heat treated to yield activated sample.

Ce-MOF-808 Base material. A solution of cerium ammonium nitrate and formic acid in DMF was combined with a solution of BTC linker in DMF. The solution was placed in an oven and heated to a suitable temperature for the formation of the MOF structure. The MOF precipitate was collected by centrifugation and washed with of fresh solvent and heat treated to yield activated sample.

Example of an oxyanion-modified metal-organic framework: $Zr-MOF-808-SO_4$. Zr-MOF-808 was immersed in a solution of sulfuric acid. The mixture was allowed to react for a suitable amount of time and the solids were collected. The modified MOF can be washed and heat treated to yield the activated sample.

Properties:

Table 5 below depicts the energy dispersive X-ray spectroscopy data of element distribution and relative composition of a samples surface.

TABLE 5

| $Zr-MOF-808-SO_4$ | | | | | |
|---|---|---|---|---|---|
| Element | C | O | S | Zr | Hf |
| Atomic % | 55.7 | 35.7 | 1.7 | 6.7 | 0.1 |
| Atoms/node | 49.8 | 32.0 | 1.5 | 6.0 | 0.1 |
| $Zr-MOF-808-PO_4$ | | | | | |
| Element | C | O | P | Zr | Hf |
| Atomic % | 59.2 | 32.4 | 0.3 | 6.8 | 0.1 |
| Atoms/node | 52.5 | 28.8 | 0.3 | 6.0 | 0.1 |
| $Hf-MOF-808-SO_4$ | | | | | |
| Element | C | O | S | Hf | |
| Atomic % | 51.8 | 37.2 | 2.8 | 8.2 | |
| Atoms/node | 38.0 | 27.3 | 2.1 | 6.0 | |
| $Hf-MOF-808-PO_4$ | | | | | |
| Element | C | O | P | Hf | |
| Atomic % | 52.9 | 38.1 | 0.1 | 8.9 | |
| Atoms/node | 35.7 | 25.7 | 0.0 | 6.0 | |
| $Ce-MOF-808-SO_4$ | | | | | |
| Element | C | O | S | Ce | |
| Atomic % | 55.8 | 35.5 | 0.6 | 8.1 | |
| Atoms/node | 41.3 | 26.3 | 0.4 | 6.0 | |

TABLE 5-continued

| $Ce-MOF-808-PO_4$ | | | | |
|---|---|---|---|---|
| Element | C | O | P | Ce |
| Atomic % | 56.6 | 35.3 | 0.0 | 8.1 |
| Atoms/node | 41.8 | 26.1 | 0.0 | 6.0 |

Catalytic Tests for Oxyanion-modified Metal-Organic Frameworks—Oligomerization

Figure 24:
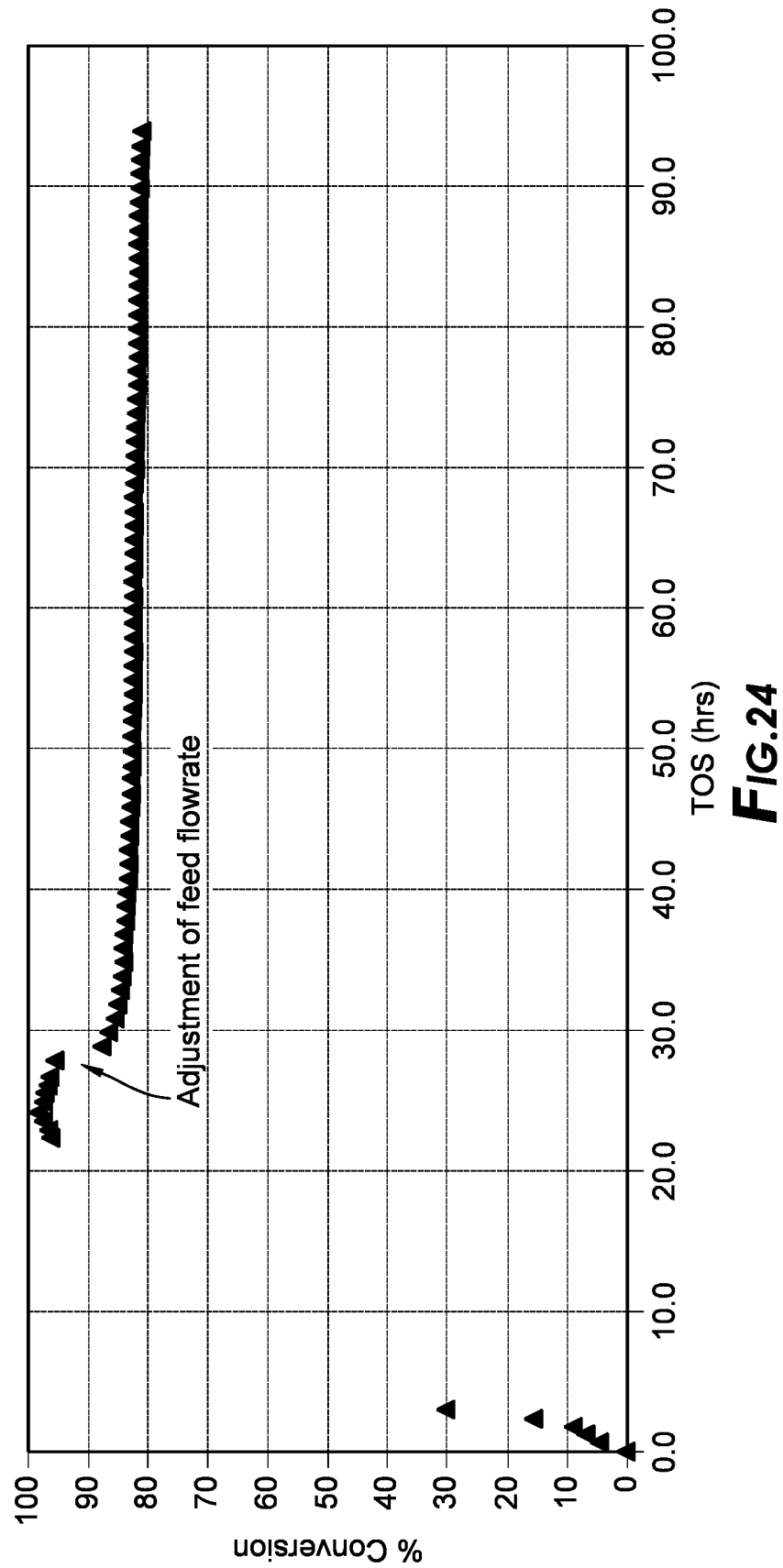
FIG. 24 depicts the conversion results.

Catalytic testing procedure: a plug-flow reactor was loaded with oxyanion-modified metal-organic framework mixed with a diluent. Prior to testing the catalyst was heat treated overnight under a flow of nitrogen. The reactor was pressurized using an inert reagent such as isobutane prior to flowing the feed. The temperature was controlled using a clam furnace. Flow of premixed isobutene/isobutane feed was achieved via a pump at a suitable rate for the appropriate time. See FIG. 24 for an example of conversion as a function of time on stream.

Figure 25:
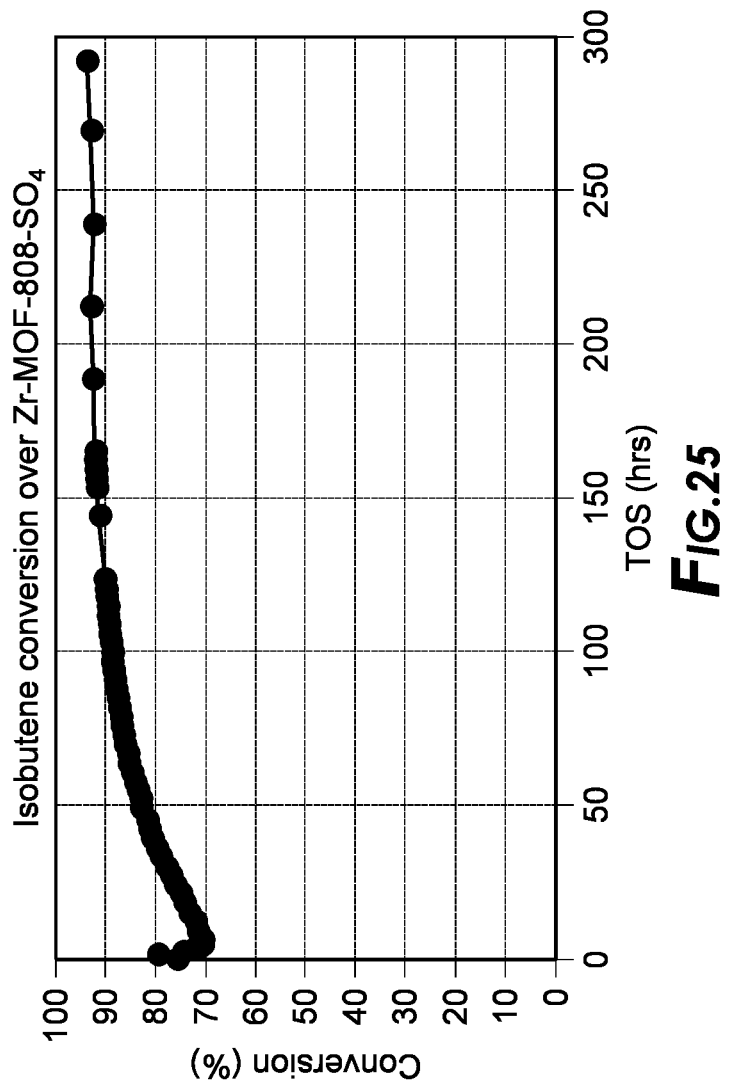
FIG. 25 depicts long term stability results.

Additional testing of the $Zr-MOF-808-SO_4$ catalyst in the plug-flow reactor for over 300 hours is shown in FIG. 25 wherein the MOF material is capable of achieving high conversion without deactivation for long periods of time. It is theorized that, the MOF architecture allows for $C_8$ and $C_{12}$ product to evacuate the channels and pores of the catalyst without being permanently trapped due to the high surface area and large pore size of the material.

Figure 26:
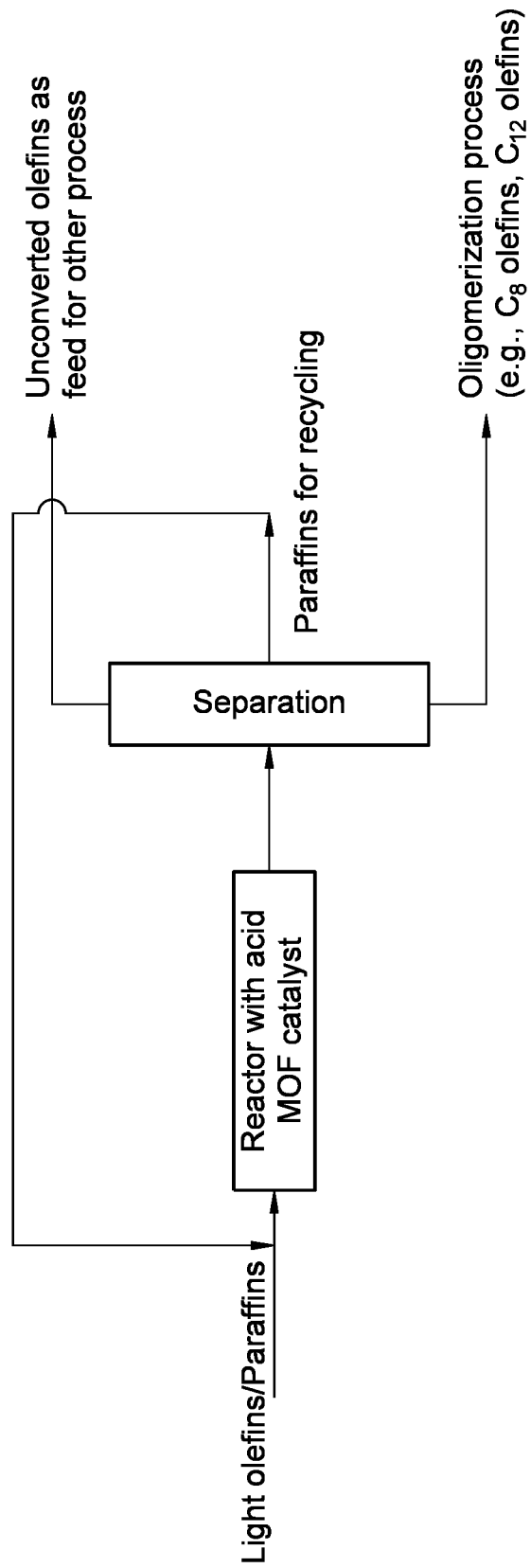
FIG. 26 depicts a non-limiting embodiment of the process.

As shown in FIG. 26, this process utilizes a fixed-bed reactor which contains a bed of MOF material to convert a stream of mixed isobutene into liquid products that are separated from the unconverted or light material. The liquid product contains a mixture of only $C_8$ olefins and $C_{12}$ olefins which can be separated further into two individual streams or be used as a mixture.

Table 6 below lists the conditions used in this experiment and shows that the reaction can proceed under mild conditions. The presence of pressurized isobutane is designed to enable higher molecular weight molecules to be removed from the surface of the catalyst to prevent catalyst deactivation by active site fouling. It is anticipated that the selectivity of the product towards $C_8$s or $C_{12}$s can be controlled by control of the space velocity (WHSV) and the concentration of olefin in the feed. We expect that higher concentration of olefin and lower space velocities will favor $C_{12}$s because the increased residence time in the catalyst will allow for more olefins to be in close contact leading to higher rate of oligomerization reactions to occur. In contrast, at higher WHSV values and more diluted $C_4$ olefin feed, $C_8$s will tend to be favored due to the lower number of olefin-olefin encounters.

TABLE 6

| Testing conditions used to generate data. | |
|---|---|
| Parameters | Value |
| Feed | Isobutane and Isobutene |
| Olefin content | 6.7% |
| Temperature | 80° C. |
| Pressure | 300 psi |
| WHSV(olefin) | 0.4 |

Analysis of the product effluent and the collection times are listed in Table 7. The high selectivity toward $C_8$ and $C_{12}$ olefins is theorized to be from a combination of factors such as large pore size and narrow acidity range of the catalyst active sites.

TABLE 7

Composition of the effluent stream demonstrating the high selectivity for $C_8$ olefins and $C_{12}$ olefins product and low heavy impurity.

| | Sample 1 | Sample 2 | Sample 3 |
|---|---|---|---|
| Time on Stream (h) | 143 | 167 | 191 |
| Conversion | 89% | 92% | 92% |
| Product Selectivity (wt %) | | | |
| $C_8$ olefins | 41.1% | 40.0% | 38.9% |
| $C_{12}$ olefins | 58.5% | 59.7% | 60.7% |
| $C_{16+}$ olefins | 0.4% | 0.2% | 0.4% |

In this example different MOF's with different pore sizes were used for light olefin oligomerization. MOF-808 with a pore size of 14 Å, PCN-777 with a pore size of 32 Å, and NU-1000 with a pore size of 32 Å were tested.

Figure 27:
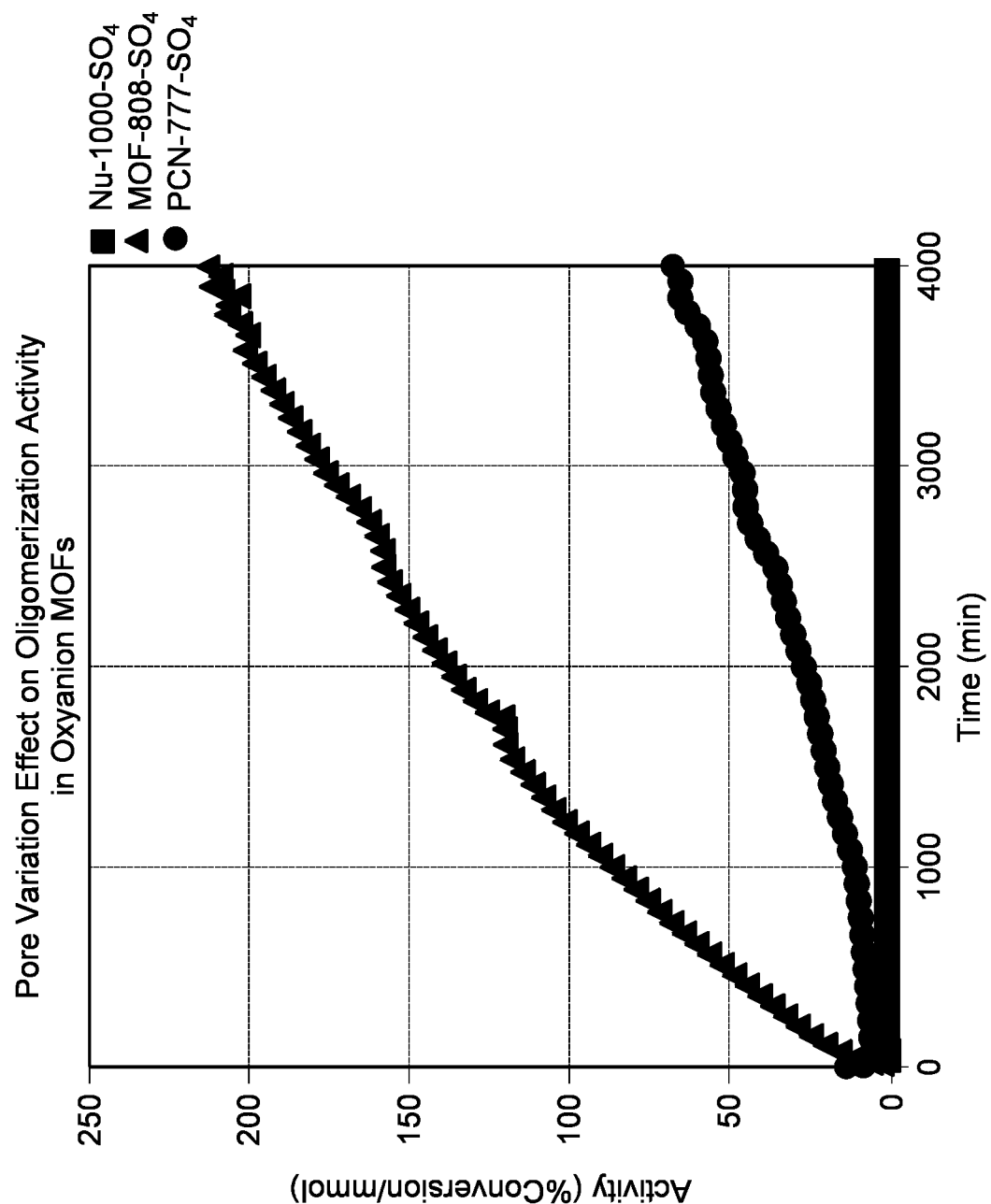
FIG. 27 depicts oligomerization results.

FIG. 27 depicts oligomerization completion rates in these various sulfated MOFs.

Table 8 below describes the pore variation effect on oligomerization activity in oxyanion MOFs

TABLE 8

| Molecule (mol %) | MOF-808-$SO_4$ | PCN-777-$SO_4$ |
|---|---|---|
| $C_8$ Olefin | 94.2 | 92.3 |
| $C_{12}$ Olefin | 4.7 | 7.5 |
| $C_{12+}$ Olefin | 0.1 | 0.2 |

In closing, it should be noted that the discussion of any reference is not an admission that it is prior art to the present invention, especially any reference that may have a publication date after the priority date of this application. At the same time, each and every claim below is hereby incorporated into this detailed description or specification as an additional embodiment of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:

1. A process comprising:
a heterogenous reaction between a solid metal organic framework supported heteropolyacid catalyst and a hydrocarbon feed to form a modified hydrocarbon stream, wherein the modified hydrocarbon stream comprises of C6+ hydrocarbons.

2. The process of claim 1, wherein the solid metal organic framework supported heteropolyacid was prepared from solution impregnation of a heteropolyacid onto a metal organic framework.

3. The process of claim 1, wherein the solid metal organic framework supported heteropolyacid was prepared from a one pot synthesis of a heteropolyacid and a metal organic framework precursor solution.

4. The process of claim 1, wherein the heterogenous reaction is an alkylation reaction.

5. The process of claim 1, wherein the heterogenous reaction is an oligomerization reaction.

6. The process of claim 1, wherein the hydrocarbon feed is selected from the group consisting of a gaseous hydrocarbon feed, a liquid hydrocarbon feed, or a supercritical hydrocarbon feed.

7. The process of claim 1, wherein the process is able to achieve a conversion to $C_{6+}$ hydrocarbons greater than 30%.

8. The process of claim 1, wherein the process is able to achieve a selectivity of $C_{6+}$ hydrocarbons greater than 30%.

9. The process of claim 1, wherein the heteropolyacid loading on the solid metal organic framework supported heteropolyacid is greater than 35% by weight.

10. The process of claim 1, wherein the pore volume of the solid metal organic framework supported heteropolyacid is less than 2 mL/g.

11. The process of claim 1, wherein the BET surface area of the solid metal organic framework supported heteropolyacid is less than 4,500 $m^2/g$.

12. The process of claim 1, wherein the hydrocarbon feed comprises essentially of $C_2$ to $C_5$ hydrocarbons.

13. A process comprising:
a heterogeneous reaction between a solid metal organic framework supported heteropolyacid and a liquid hydrocarbon feed, consisting essentially of $C_2$ to $C_5$ hydrocarbons, to form a modified hydrocarbon stream; wherein the modified hydrocarbon stream comprises of $C_{6+}$ hydrocarbons.

* * * * *